(12) United States Patent
Woodsum et al.

(10) Patent No.: US 11,304,661 B2
(45) Date of Patent: Apr. 19, 2022

(54) ENHANCED IMAGING DEVICES, AND IMAGE CONSTRUCTION METHODS AND PROCESSES EMPLOYING HERMETIC TRANSFORMS

(71) Applicant: VertoCOMM, Inc., Weston, MA (US)

(72) Inventors: Harvey C. Woodsum, Bedford, NH (US); Christopher M. Woodsum, Bedford, NH (US)

(73) Assignee: VERTOCOMM, INC., Weston, MA (US)

(*) Notice: Subject to any disclaimer, the term of this patent is extended or adjusted under 35 U.S.C. 154(b) by 0 days.

(21) Appl. No.: 14/921,893

(22) Filed: Oct. 23, 2015

(65) Prior Publication Data

US 2016/0189374 A1 Jun. 30, 2016

Related U.S. Application Data

(60) Provisional application No. 62/067,591, filed on Oct. 23, 2014.

(51) Int. Cl.
| | | |
|---|---|---|
| *A61B 5/00* | (2006.01) | |
| *G06K 9/52* | (2006.01) | |
| *A61B 5/055* | (2006.01) | |
| *G06T 11/00* | (2006.01) | |
| *A61B 6/03* | (2006.01) | |
| *A61B 6/00* | (2006.01) | |

(52) U.S. Cl.
CPC ............ *A61B 5/7253* (2013.01); *A61B 5/055* (2013.01); *G06K 9/522* (2013.01); *G06T 11/005* (2013.01); *A61B 5/7225* (2013.01); *A61B 6/032* (2013.01); *A61B 6/483* (2013.01); *A61B 6/5205* (2013.01); *G06T 2211/421* (2013.01)

(58) Field of Classification Search
None
See application file for complete search history.

(56) References Cited

U.S. PATENT DOCUMENTS

| | | |
|---|---|---|
| 4,338,605 A | 7/1982 | Mims |
| 4,989,090 A | 1/1991 | Campbell et al. |

(Continued)

FOREIGN PATENT DOCUMENTS

| | | | |
|---|---|---|---|
| CN | 103153330 A | 6/2013 | |
| WO | WO 2013/134506 | * 9/2013 | ............... H04B 1/10 |

OTHER PUBLICATIONS

Doblinger, G., "Beamforming with Optimized Interpolated Microphone Arrays," IEEE HSCMA Conference Proceedings, pp. 33-36 (2008).

(Continued)

*Primary Examiner* — Vikkram Bali
(74) *Attorney, Agent, or Firm* — Wilmer Cutler Pickering Hale and Dorr LLP

(57) ABSTRACT

In an exemplary embodiment, a tomography device comprises a scanner that obtains image slices. The device additionally comprises at least one processor configured to: perform a Hermetic Transform on the image slices to obtain hermetically transformed data using; filter and perform an Inverse Hermetic Transform on the Hermetic Transform data to obtain filtered inverse Hermetic Transform data; and perform back projection and angle integration on the filtered inverse Hermetic Transform data.

37 Claims, 19 Drawing Sheets

(56) References Cited

U.S. PATENT DOCUMENTS

| | | | |
|---|---|---|---|
| 5,479,176 | A | 12/1995 | Zavrel, Jr. |
| 5,583,884 | A | 12/1996 | Maruyama et al. |
| 5,892,847 | A | 4/1999 | Johnson |
| 5,933,537 | A | 8/1999 | Hajjahmad et al. |
| 6,101,399 | A | 8/2000 | Raleigh et al. |
| 6,185,440 | B1 | 2/2001 | Barratt et al. |
| 6,229,486 | B1 | 5/2001 | Krile |
| 6,317,612 | B1 | 11/2001 | Farsakh |
| 6,408,109 | B1 | 6/2002 | Silver et al. |
| 6,421,007 | B1 | 7/2002 | Owen et al. |
| 6,427,531 | B1 | 8/2002 | Chintawongvanich |
| 6,441,786 | B1 | 8/2002 | Jasper et al. |
| 6,606,058 | B1 | 8/2003 | Bonek et al. |
| 6,876,693 | B2 | 4/2005 | Sim |
| 6,943,732 | B2 | 9/2005 | Gottl et al. |
| 6,947,470 | B2 | 9/2005 | Berens |
| 7,012,978 | B2 | 3/2006 | Talwar |
| 7,065,070 | B1 | 6/2006 | Chang |
| 7,092,690 | B2 | 8/2006 | Zancewicz |
| 7,103,537 | B2 | 9/2006 | Witzgall et al. |
| 7,106,785 | B2 | 9/2006 | Yoshida |
| 7,260,370 | B2 | 8/2007 | Wang et al. |
| 7,280,627 | B2 | 10/2007 | Orlin |
| 7,298,805 | B2 | 11/2007 | Walton et al. |
| 7,415,711 | B2 | 8/2008 | Chew et al. |
| 7,443,942 | B2 | 10/2008 | Kouyama |
| 7,450,067 | B2 | 11/2008 | Xin |
| 7,873,016 | B2 | 1/2011 | Kim |
| 7,925,234 | B2 | 4/2011 | Yeh et al. |
| 8,005,162 | B2 | 8/2011 | Cai et al. |
| 8,036,287 | B2 | 10/2011 | Hwang et al. |
| 8,064,408 | B2 | 11/2011 | Woodsum |
| 8,363,704 | B1 | 1/2013 | Rayburn |
| 8,433,804 | B2 | 4/2013 | Swanburg et al. |
| 8,917,786 | B1 | 12/2014 | von der Embse |
| 9,154,353 | B2 | 10/2015 | Woodsum |
| 2002/0034215 | A1 | 3/2002 | Inoue et al. |
| 2003/0039303 | A1 | 2/2003 | Sriram |
| 2003/0176196 | A1 | 9/2003 | Hall et al. |
| 2003/0216156 | A1 | 11/2003 | Chun |
| 2003/0219064 | A1 | 11/2003 | Pan et al. |
| 2004/0071200 | A1 | 4/2004 | Betz et al. |
| 2004/0095990 | A1 | 5/2004 | Gossett et al. |
| 2004/0120429 | A1 | 6/2004 | Orlin |
| 2004/0223538 | A1 | 11/2004 | Zeira |
| 2005/0013347 | A1 | 1/2005 | Pan et al. |
| 2005/0025267 | A1 | 2/2005 | Reznik et al. |
| 2005/0031024 | A1 | 2/2005 | Yang et al. |
| 2005/0101253 | A1 | 5/2005 | Pajukoski et al. |
| 2005/0128937 | A1 | 6/2005 | Akopian |
| 2005/0141545 | A1 | 6/2005 | Fein et al. |
| 2005/0200515 | A1 | 9/2005 | Cherniakov |
| 2005/0271016 | A1 | 12/2005 | Kim et al. |
| 2006/0013332 | A1 | 1/2006 | Rayburn |
| 2006/0030364 | A1 | 2/2006 | Olesen et al. |
| 2006/0053005 | A1 | 3/2006 | Gulati |
| 2006/0244660 | A1 | 11/2006 | Ann et al. |
| 2007/0001897 | A1 | 1/2007 | Alland |
| 2007/0071071 | A1 | 3/2007 | Li et al. |
| 2007/0164902 | A1 | 7/2007 | Bang et al. |
| 2007/0189362 | A1 | 8/2007 | D'Amico et al. |
| 2007/0213013 | A1 | 9/2007 | Kim |
| 2008/0129584 | A1 | 6/2008 | Antonik et al. |
| 2008/0260066 | A1 | 10/2008 | Cai et al. |
| 2008/0317172 | A1 | 12/2008 | Zhang et al. |
| 2009/0237294 | A1 | 9/2009 | Shoji et al. |
| 2009/0239551 | A1 | 9/2009 | Woodsum |
| 2010/0178057 | A1 | 7/2010 | Shieh |
| 2010/0254325 | A1 | 10/2010 | Narasimhan et al. |
| 2010/0272005 | A1 | 10/2010 | Larsson et al. |
| 2010/0303182 | A1 | 12/2010 | Daneshrad et al. |
| 2011/0069774 | A1 | 3/2011 | Wang et al. |
| 2011/0182577 | A1 | 7/2011 | Wu |
| 2011/0187702 | A1* | 8/2011 | Schwartz ............... 345/419 |
| 2011/0188597 | A1 | 8/2011 | Agee et al. |
| 2011/0288823 | A1 | 11/2011 | Gupta |
| 2012/0027111 | A1 | 2/2012 | Vook et al. |
| 2012/0064916 | A1 | 3/2012 | Woodsum |
| 2012/0188058 | A1 | 7/2012 | Lee et al. |
| 2012/0212371 | A1 | 8/2012 | Chang |
| 2012/0262328 | A1 | 10/2012 | Shinonaga et al. |
| 2013/0116561 | A1 | 5/2013 | Rothberg et al. |
| 2013/0252568 | A1 | 9/2013 | Woodsum |
| 2013/0344909 | A1 | 12/2013 | Davydov et al. |
| 2014/0064403 | A1 | 3/2014 | Woodsum |
| 2015/0117497 | A1 | 4/2015 | Woodsum |
| 2015/0145716 | A1 | 5/2015 | Woodsum |
| 2016/0142239 | A1 | 5/2016 | Woodsum |
| 2016/0189374 | A1 | 6/2016 | Woodsum et al. |
| 2016/0211906 | A1 | 7/2016 | Woodsum |

OTHER PUBLICATIONS

Extended European Search Report issued by the European Patent Office for European Patent Application No. 13824997.4 dated Apr. 14, 2016 (8 pages).

Gabel and Roberts, "Signals and Linear Systems", 2nd Edition, John Wiley & Sons, New York, pp. 327-332, 345 (1980) (9 total pgs.).

Goshi, et al., "A Compact Digital Beamforming SMILE Array for Mobile Communications," IEEE Transactions on Microwave Theory and Techniques, vol. 52, No. 12, 7 pgs. (Dec. 2004).

International Search Report and Written Opinion issued by the U.S. Patent and Trademark Office as International Searching Authority for International Application No. PCT/US14/62211 dated Feb. 3, 2015 (8 pgs.).

International Search Report and Written Opinion issued by the U.S. Patent and Trademark Office as International Searching Authority for International Application No. PCT/US14/67148 dated Jul. 31, 2015 (11 pgs.).

International Search Report and Written Opinion issued by the U.S. Patent and Trademark Office as International Searching Authority in International Application No. PCT/US09/034264 dated Apr. 23, 2009 (11 pgs.).

International Search Report and Written Opinion issued by the U.S. Patent and Trademark Office as International Searching Authority in International Application No. PCT/US13/29613 dated May 8, 2013 (8 pages).

International Search Report and Written Opinion issued by the U.S. Patent and Trademark Office as International Searching Authority in International Application No. PCT/US13/53422 dated Oct. 4, 2013 (7 pgs.).

Koch, et al., "Increased Capacity per Unit-cost by Oversampling," arxiv. org., Cornell University Library, Ithaca, NY, 27 pages (Aug. 31, 2010).

Monzingo and Miller, "Introduction to Adaptive Arrays", John Wiley & Sons, New York p. 274 Chapters (Total 78 pgs.) (1980).

Pinchon, et al., "A Design Technique for Oversampled Modulated Filter Banks and OFDM/QAM Modulations," in Lecture Notes in Computer Science, Springer Berlin Heidelberg, Berlin, Heidelberg, 10 pages (Jan. 1, 2004).

Rao, C.R., "Estimation of Variance and Covariance Components in Linear Models," J. Americ. Stat. Assoc., Issue 337, pp. 112-115 (Mar. 1972) (Published on line Apr. 5, 2012).

Woodsum, C.M. and Woodsum, H.C., "Optimization of Cascaded Hermetic Transform Processing Architectures via a Chimerical-Hybrid Genetic Algorithm," Proceedings of the Sixteenth International Conference on Cognitive and Neural Systems (ICCNS), Boston University, May 30-Jun. 1, 2012 (1 page).

Zhang, et al., "An Oversampled Filter Bank Multicarrier System for Cognitive Radio," 2008 IEEE 19th International Symposium on Personal, Indoorand Mobile Radio Communications. IEEE, 2008 5 pages (Sep. 15, 2008).

\* cited by examiner

| | T1 (ms) 0.25 T | T1 (ms) 0.5 T | T1 (ms) 1 T | T1 (ms) 1.5 T | 8D (%) | T2 (ms) | 8D (%) |
|---|---|---|---|---|---|---|---|
| BRAIN | | | | | | | |
| Gray matter | 530 | 657 | 813 | 921 | 17 | 101 | 13 |
| White matter | 422 | 537 | 683 | 787 | 17 | 92 | 22 |
| Tumours | 667 | 802 | 963 | 1073 | 36 | 121 | 63 |
| Meningloma | 586 | 714 | 871 | 979 | 18 | 103 | 31 |
| Glioma | 845 | 887 | 931 | 959 | 35 | 111 | 33 |
| Edema | 667 | 806 | 973 | 1090 | 23 | 113 | 73 |
| BONE | | | | | | | |
| Normal marrow | 607 | 648 | 695 | 732 | 78 | 106 | 60 |
| Osteosarcoma | 740 | 811 | 888 | 973 | 28 | 95 | 30 |
| BREAST | | | | | | | |
| Fibrotic tissue | 409 | 547 | 732 | 868 | 18 | 49 | 16 |
| Adipose tissue | 190 | 214 | 241 | 259 | 28 | 94 | 36 |
| Tumours | 483 | 634 | 832 | 976 | 28 | 90 | 35 |
| Carcinoma | 451 | 595 | 785 | 923 | 25 | 94 | 48 |
| Adenocarcinoma | 490 | 686 | 959 | 1157 | 10 | 91 | 12 |
| Fibroadenoma | 508 | 715 | 989 | 1195 | 29 | 60 | 11 |
| KIDNEY | | | | | | | |
| Normal tissue | 417 | 496 | 589 | 652 | 27 | 58 | 24 |
| Tumours | 733 | 796 | 864 | 907 | 37 | 83 | 42 |
| LIVER | | | | | | | |
| Normal tissue | 250 | 325 | 423 | 493 | 22 | 43 | 14 |
| Tumours | 713 | 782 | 857 | 905 | 26 | 84 | 31 |
| Hepatoma | 621 | 769 | 951 | 1077 | 16 | 94 | 26 |
| Chimosis | 328 | 367 | 410 | 438 | 21 | 45 | |
| LUNG | | | | | | | |
| Normal tissue | 488 | 599 | 735 | 829 | 19 | 79 | 29 |
| Tumours | 407 | 535 | 703 | 826 | 51 | 58 | 45 |
| MUSCLE | | | | | | | |
| Normal tissue | 409 | 547 | 732 | 868 | 18 | 47 | 13 |
| Tumours | 597 | 752 | 946 | 1083 | 32 | 87 | 40 |
| Carcinoma | 608 | 750 | 925 | 1046 | 16 | 92 | 73 |
| Fibrosarcoma | 831 | 896 | 967 | 1011 | 15 | 65 | 14 |
| Rhabdomyosarcoma | 664 | 827 | 1031 | 1173 | 27 | | |
| Edema | 652 | 897 | 1235 | 1488 | 26 | 67 | 26 |
| PANCREAS | | | | | | | |
| Normal tissue | 302 | 371 | 455 | 513 | 25 | | |
| Tumours | 718 | 942 | 1235 | 1443 | 15 | | |
| SPLEEN | | | | | | | |
| Normal tissue | 431 | 543 | 683 | 782 | 19 | 62 | 27 |
| Tumours | | | | | | 69 | 1 |

FIG. 8

ENHANCED IMAGING DEVICES, AND IMAGE CONSTRUCTION METHODS AND PROCESSES EMPLOYING HERMETIC TRANSFORMS

CROSS-REFERENCE TO RELATED APPLICATIONS

The present application claims the benefit of U.S. Patent Application No. 62/067,591, filed on Oct. 23, 2014, the content of which is hereby incorporated by reference herein in its entirety.

TECHNICAL FIELD

This technology relates generally to imaging and hermetic transforms. In particular, aspects of this invention relate to enhanced imaging devices, and image construction methods and processes employing hermetic transforms.

BACKGROUND

Modern medicine includes a number of types of imaging techniques and devices which are used to locate and identify pathology and various forms of injury in the body. For example, such techniques and devices include tomographic imaging systems, Magnetic Resonance Imaging (MRI) machines, and ultrasonic imaging devices, among others.

An increase in image resolution and other improvements are sought in order to improve the utility of such devices and techniques.

SUMMARY

According to one or more embodiments, a tomography device comprises a scanner that obtains at least one image slice; and at least one processor configured to: perform a Hermetic Transform on the at least one image slice to obtain hermetically transformed data; filter and perform an Inverse Hermetic Transform on the Hermetic Transform data to obtain filtered inverse Hermetic Transform data; and perform back projection and angle integration on the filtered inverse Hermetic Transform data.

In one or more embodiments, the scanner obtains the at least one image slice through at least one of X-Ray imaging, radioactive emission imaging, Positron Emission imaging, sonic imaging, ultrasonic imaging, Magnetic Resonance Imaging, Nuclear Quadropole Imaging, or Electron Paramagnetic Imaging. In further exemplary embodiments, the scanner obtains the at least one image slice through at least one of measuring attenuation of radiation, measuring time of flight radiation, or measuring forward scatter diffraction.

In one or more embodiments, a method of obtaining a tomographic image comprises obtaining at least one image slice; performing a Hermetic Transform on the at least one image slice to obtain hermetically transformed data; filtering and performing an Inverse Hermetic Transform on the Hermetic Transform data to obtain filtered inverse Hermetic Transform data; and performing back projection and angle integration on the filtered inverse Hermetic Transform data.

In one or more embodiments, the at least one image slice comprises using at least one of X-Ray imaging, radioactive emission imaging, Positron Emission imaging, sonic imaging, ultrasonic imaging, Magnetic Resonance Imaging, Nuclear Quadropole Imaging, or Electron Paramagnetic Imaging. In further embodiments, obtaining the at least one image slice comprises at least one of measuring attenuation of radiation, measuring time of flight radiation, or measuring forward scatter diffraction.

In one or more embodiments, a measuring device comprises: a scanner that obtains at least one signal parameter; and at least one processor configured to perform a Hermetic Transform on the at least one signal parameter.

In one or more embodiments, the at least one signal parameter comprises frequency data; and the at least one processor is further configured to determine a position of an object using the Hermetic Transform of the at least one signal parameter. In one or more embodiments, the at least one signal parameter comprises time data; and the at least one processor is further configured to perform Hermetic Matched Filtering to locate echoes. In one or more embodiments, the at least one processor is further configured to perform motion compensation by tracking phases using the Hermetic Transform of the at least one signal parameter. In one or more embodiments, the at least one signal parameter comprises spatial data; the scanner further comprises an RF array; and the at least one processor is further configured to perform beam forming on the RF array. In one or more embodiments, obtaining the at least one signal parameter using the scanner comprises at least one of Magnetic Resonance Imaging (MIR), Electron Paramagnetic Resonance (EPRI), or Nuclear Quadrapole resonance (NQPRI).

In one or more embodiments, a method of measuring at least one signal parameter comprising: obtaining at least one signal parameter; and performing a Hermetic Transform on the at least one signal parameter.

In one or more embodiments, the at least one signal parameter comprises frequency data; and performing a Hermetic Transform on the at least one signal parameter comprises determining a position of an object. In one or more embodiments, the at least one signal parameter comprises time data; and performing Hermetic Transform on the at least one signal parameter comprises performing Hermetic Matched Filtering to locate echoes. In one or more embodiments, the method further comprises tracking phases to perform motion compensation. In one or more embodiments, the at least one signal parameter comprises spatial data; and performing Hermetic Transform on the at least one signal parameter comprises beam forming an RF array. In one or more embodiments, obtaining the at least one signal parameters comprises at least one of Magnetic Resonance Imaging (MIR), Electron Paramagnetic Resonance (EPRI), or Nuclear Quadrapole resonance (NQPRI).

In one or more embodiments, an ultrasonic imaging device comprises: an ultrasonic array and beam-former that transmits an ultrasonic signal; an ultrasonic receiving array that receives ultrasonic echoes; and at least one processor configured to perform a Hermetic Transform on the echoes.

In one or more embodiments, the at least one processor performs Hermetic Matched Filtering to obtain a propagation delay measurement. In one or more embodiments, the at least one processor performs the Hermetic Transform as a frequency analysis to obtain Doppler frequency shift measurements. In one or more embodiments, the transmitting and receiving arrays are not co-located. In one or more embodiments a filter transmits pulsed signals to enhance specific resonance modes to enhance image resolution of object characteristics.

In one or more embodiments, a method of ultrasonic imaging comprises: transmitting an ultrasonic signal; receiving ultrasonic echoes; and performing a Hermetic Transform on the echoes.

In one or more embodiments, the method further comprises performing Hermetic Matched Filtering to obtain a propagation delay measurement. In one or more embodiments, the method further comprises performing the Hermetic Transform as a frequency analysis to obtain Doppler frequency shift measurements. In one or more embodiments, the method further comprises transmitting pulsed signals to enhance specific resonance modes to enhance image resolution of object characteristics. In one or more embodiments, the method further comprises performing tomographic imaging through at least one of absorption, diffraction, or time of flight. In one or more embodiments, the method further comprises performing at least one of tissue heating, ultrasonic neuromodulation, lithotripsy, or low-intensity pulsed ultrasound.

In one or more embodiments the devices and methods, the Hermetic Transform comprises a robust Hermetic Transform. In one or more embodiments, the at least one signal parameter comprise at least one of signal location in frequency, signal location in space, signal location in time, tracking of phase variations, or tracking of decay time.

In one or more embodiments, an imaging device comprises: a scanner having a receiver array; and at least one processor configured to apply Hermetic Matched Filtering to each channel and create beams for additional spatial filtering and signal separation via a time-delay beamforming approach. In one or more embodiments, an imaging method comprises apply a Hermetic Matched Filtering to each channel of a receiver array and creating beams for additional spatial filtering and signal separation via a time-delay beamforming approach.

In one or more embodiments, the at least one signal parameter comprises a complex frequency; and the at least one processor is further configured to obtain signal decay constants using the Hermetic Transform. In further embodiments, the at least one signal parameter comprises a complex frequency; and performing a Hermetic Transform on the at least one signal parameter comprises obtaining signal decay constants.

These and other aspects and embodiments of the disclosure are illustrated and described below.

BRIEF DESCRIPTION OF THE DRAWINGS

FIG. 8 shows example tables of T1 and T2 by tissue type according to exemplary an embodiment.

DETAILED DESCRIPTION OF EXEMPLARY EMBODIMENTS

According to one or more exemplary embodiments, devices and methods are disclosed that can increase image resolution of Computerized Tomography (CT), including X-Ray Tomography, Radiation Emission Tomography, and Ultrasonic Tomography, and improve various aspects of Magnetic Resonance Imaging (MRI), Electron Paramagnetic Imaging, and related approaches, as well as Ultrasound Imaging. In the case of MRI Scanners and other devices, devices and methods according to an exemplary embodiment can be utilized to make practical devices which allow use of smaller, less expensive magnets, while maintaining the resolution of present devices. In one or more exemplary embodiments, these applications on technology can make use of Hermetic Transforms as a means of gaining resolution, and in certain exemplary embodiments, as the primary means of gaining resolution.

According to one or more exemplary embodiments, devices and methods are disclosed that overcome limitations that are imposed through the reliance on the mathematics of the Fourier Transform, these limitations being overcome through the employment of Hermetic Transforms as an alternative. According to one or more exemplary embodiments, novel and useful improvements are obtained, for example, for processing of signals received or transmitted from certain imaging and therapeutic devices by tomography, signal frequency and phase resolution, and/or beamforming, by employing Hermetic Transforms, including aspects such as signal oversampling (in time or space, according to relevance). According to one or more exemplary embodiments, additional improvements in the area of signal processing and/or device construction are obtained indirectly as a result of reduced technical limitations for engineering of such devices. Examples include the ability to construct MRI machines with smaller and less expensive magnets, and the ability to build machines having useful imaging resolution with field strengths which are improved with respect to measurement resolution per field strength.

These and other aspects of the exemplary embodiments disclosed herein are discussed in further detail below.

Modern medical tools include a number of types of imaging devices which are used to locate and identify pathology and various forms of injury in the body. An increase in image resolution is sought in order to improve the utility of such devices. In addition, techniques such as Magnetic Resonance, can be used as a form of microscopy, which also has medical application.

Figure 1:
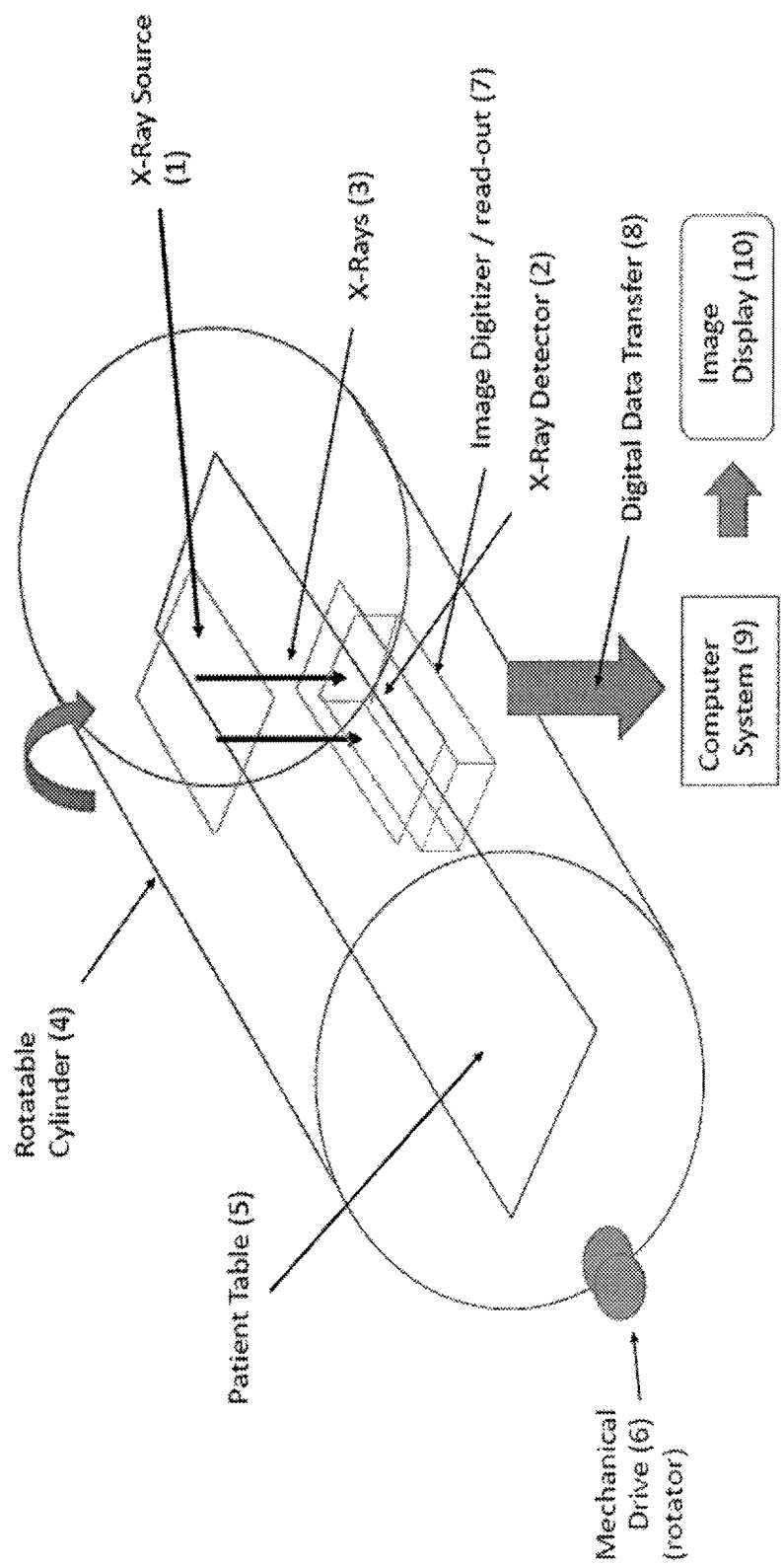
FIG. 1 illustrates a CT scanner device according to an exemplary embodiment.

FIG. 1 illustrates a scanner device according to an exemplary embodiment. A CAT (or CT) scanner comprises a device which employs a set of X-Ray image projections ("slices"), taken at various angles ($\theta$) around the body axis in order to create a full 3-D X-Ray image. Each X-Ray casts a "shadow" on a detector, the shadow related to X-Ray absorption on the path between the X-Ray source and detector.

In an exemplary embodiment, the creation of a 3-D image from a set of 2-D images uses "tomographic back-projection," which in turn uses the Projection Slice Theorem. The X-Ray CT device, for example, collects a set of X-Ray images at different orientations with respect to the object and assembles from these a three-dimensional (3-D) image. In further exemplary embodiments, the scanners use radioactive materials consumed by or otherwise placed within the patient. The radiation is emitted from within the body, and is then detected externally from various directions in order to form the "slice" images. An example of the latter is the PET scanner.

In FIG. 1, an X-Ray source (1) is mountable on a rotatable mechanical assembly (e.g., a cylindrical drum) (4) which is mounted directly opposite an X-Ray detector (2). The X-Rays generated by the source propagate through the object being scanned (e.g., a human body) as shown (3). The patient being scanned rests on a table (5). The drum upon which the X-Ray source and detector are mounted is rotated mechanically by a drive mechanism (6). By rotating the X-Ray source/detector arrangement at a particular angles {θi} image projections (slice images) are created. The detector output is converted to digital form (7) so that each slice image can be stored. The digitized data is then supplied to a computer system which performs an algorithm that creates, from the slices, a 2-D image for each position along the body axis. These 2-D images are then assembled to form the full 3-D image. Any number of means of obtaining slice images for tomographic reconstruction can be implemented; the exemplary embodiment shown is not meant to restrict the means of obtaining image slice data. In an exemplary embodiment, a scanner such as the CT scanner of FIG. 1 can be used with the Hermetic Transformed tomography, discussed further below.

Figure 2:
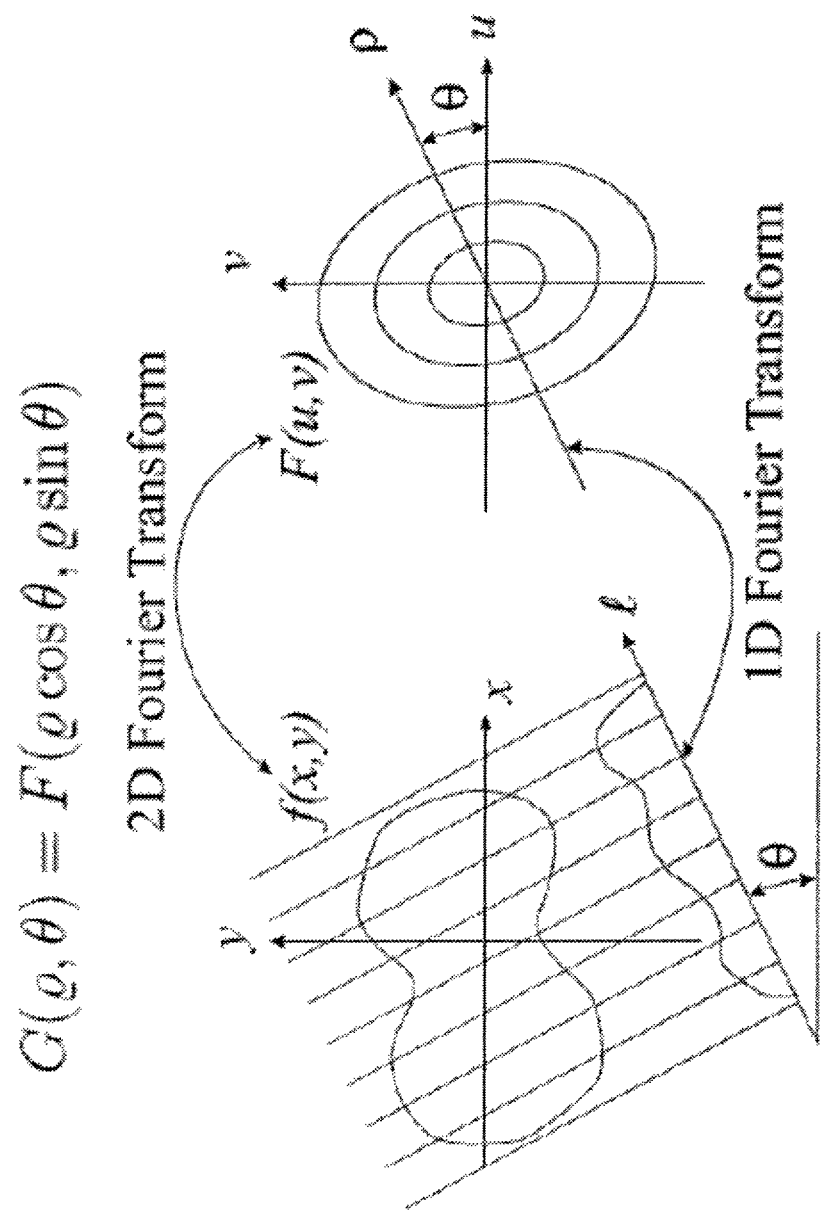
FIG. 2 shows an illustration of the Projection Slide Theorem according to an exemplary embodiment.

According to an exemplary embodiment, the methods and systems described here use a new and higher resolution approach for reconstructing CT images tomographically. This reconstruction can be performed within the computer system portion of the device. For example, in an exemplary embodiment, a digital computer would be used to perform the reconstruction algorithm. In further exemplary embodiments, any method (including analog computing) for accomplishing the same steps could be used. According to the Projection Slice Theorem, the Fourier Transform of each of the "slice" images is a corresponding "slice" (at the same physical angle) of the Fourier Transform of the dimensional function being projected. The Projection Slice Theorem is illustrated in FIG. 2. In FIG. 2, the CT axis is oriented so as to be into the page. FIG. 2 shows an example illustrating that the Fourier Transform of each of the "slice" images is a corresponding "slice" (at the same physical angle) of the Fourier Transform of the dimensional function being projected. In an exemplary embodiment, the Projection Slice Theorem can be used with the Hermetic Transformed tomography, discussed further below.

In an exemplary embodiment, the "slice images" can be Fourier Transformed, resampled on a uniformly spaced grid, and then inverse Fourier Transformed to create a full image of the object (e.g., the human body) being examined. The Radon Transform and various types of filters can also utilized within CT scanners; however, tomographic reconstruction is mathematically related to the Projection Slice Theorem and therefore to the Fourier Transform.

Figure 3:
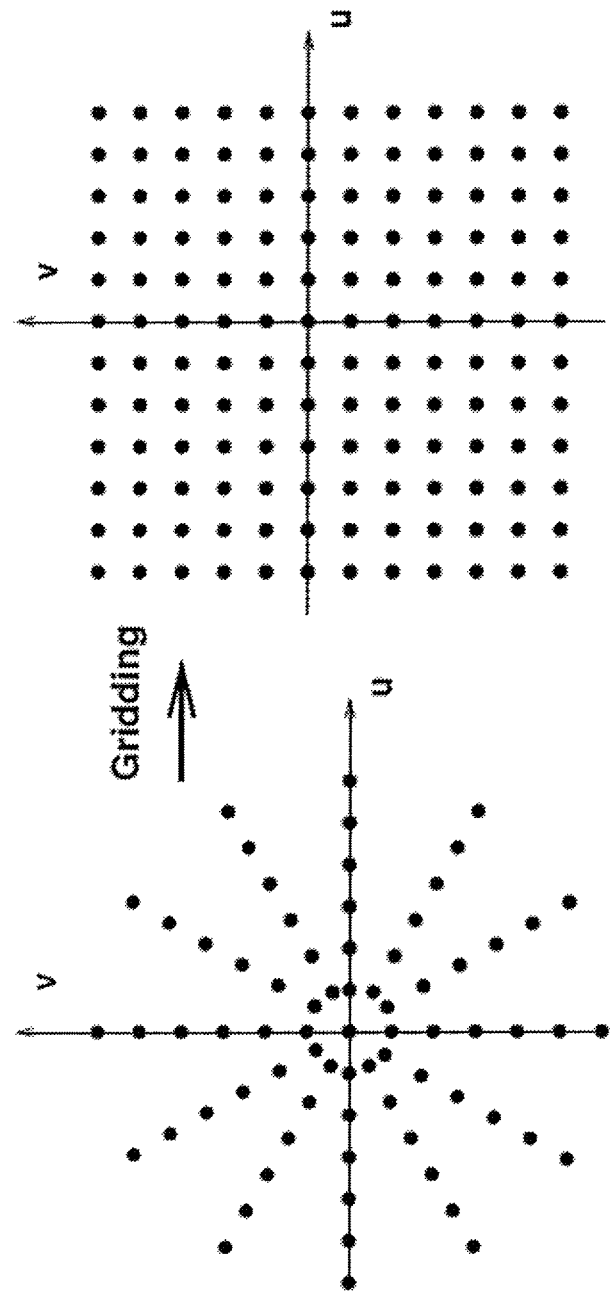
FIG. 3 shows an illustration of the conversion of "slices" of the object response Fourier Transform (which lie along radials at various angles) into a rectangular grid so that a Fourier Transform can be utilized in the reconstruction according to an exemplary embodiment.

FIG. 3 shows an illustration of the conversion of "slices" of the object response Fourier Transform (which lie along radials at various angles) into a rectangular grid so that a Fourier Transform can be utilized in the reconstruction according to an exemplary embodiment. In an exemplary embodiment, the slices samples in the frequency domain can also be obtained through a Hermetic Transform, as discussed further below.

Figure 4:
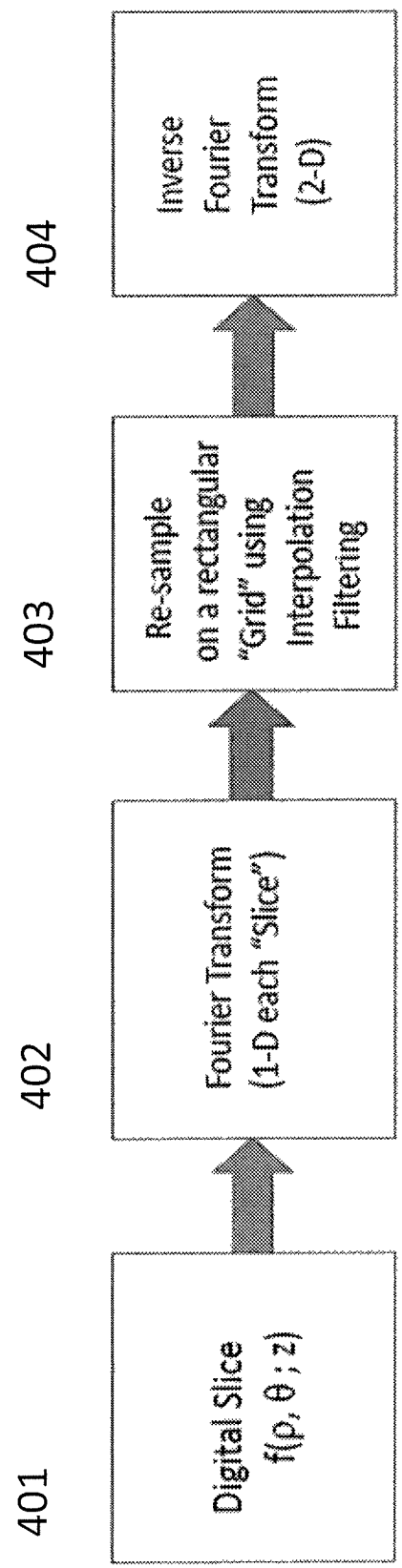
FIG. 4 shows direct method of tomographic image construction according to an exemplary embodiment.

A direct method of tomographic image construction according to an exemplary embodiment is shown in FIG. 4. To summarize, in an exemplary embodiment, the direct method makes use of Fourier Transforms of a collection of digital slices, each of which is a function of the linear projection dimension (ρ) and the rotation angle θ, as well as the position of the slice in the axial dimension (z), as illustrated in 401 and 402. The method re-samples these slices on a uniform grid, and then inverse Fourier Transforms back to the spatial domain to create a set of volume-image cells ("voxels"), as illustrated in 403 and 404. In further embodiments, other means of performing the same functions can be incorporated in CT scanners. These alternative methods can be preferentially adopted due to the higher quality of image produced in a practical sense.

Briefly, the following derivation shows how the Filtered Back Projection Algorithm is derived in terms of the above mathematics according to an exemplary embodiment. Along one axial position z, the fundamental image f(x, y) represents the absorption coefficient of the object as a function of position (x, y). This image can be written in terms of the two-dimensional Fourier Transform.

$$f(x,y) = \int_{-\infty}^{\infty}\int_{-\infty}^{\infty} dv_y dv_x F(v_x, v_y) e^{-j2\pi v_x x} e^{-j2\pi v_y y}$$

where the Greek letter v is used to denote spatial frequency. If one considers the form of the above integral in polar coordinates, the following expression obtains:

$$f(x,y) = \int_0^{\pi} d\phi \int_{-\infty}^{\infty} dv |v| P(v,\phi) e^{-j2\pi v(x \cos\phi + y \sin\phi)}$$

Where P(v,φ) is the 1-D Fourier Transform projected onto a line at angle φ.

$$P(v,\phi) = F(v \cos\phi, v \sin\phi).$$

The integral of n can be done in close form leading to:

$$\int_0^{\pi} d\phi p'(x \cos\phi + y \sin\phi, \phi)$$

Here p' is defined in terms of a ramp filter in the frequency domain and the 1-D inverse Fourier Transform, $$p'(\xi,\phi) = \int_{-\infty}^{\infty} |v| P(v,\phi) e^{-j2\pi v\xi} dv$$

According to an exemplary embodiment, tomographic techniques based on this very same Projection Slice Theorem can be utilized in Diffraction Tomography, where the wavelength of the radiation used is such that diffraction as well as absorption needs to be taken into account; for example, in ultrasound, and for microwave forms.

In an exemplary embodiment, Hermetic Transforms can be utilized. Hermetic Transforms are mathematically analogous to Fourier Transforms and can be used in place of the Fourier Transform in the figures and equations above. One difference is that the Hermetic Transform can create optimal resolution from sampled data (e.g., the signal) that is over-sampled as compared to the Nyquist Rate. In an exemplary embodiment, Hermetic Transforms can be utilized in CT scanning in place of Fourier-based processing to create substantially higher resolution. As applied to CT scanning, exemplary embodiments of these methods improve upon systems employing a Fourier Transformer by replacing the Fourier Transformer related portion of a CT scanner, with a Hermetic Transformer. In such exemplary embodiments, the projection-slice property still applies (therefore tomographic reconstruction works the same way) while the Hermetic Transform offers the benefit of higher resolution in converting slices to the spatial frequency ("K-Space") domain.

In an exemplary embodiment, to construct a spatial Hermetic Transform, a "manifold matrix" $\underline{\Sigma}$ is formed as a matrix of column vectors where each column vector is a complex sinusoidal signal computed with spatial samples that are multiples of the spatial sampling interval $L_s$, where $L_s=1/K_s$, Ks being the linear wavenumber sampling frequency. A set of M spatial frequencies ($K_m$) are employed in the transform. The "manifold" element for row—n and column—m is given by:

$$\underline{\Sigma}(n,m) = \exp[i\, K_m n\, L_s]$$

The equation used to develop the Hermetic Transform $\underline{H}$ from the manifold matrix (as contained in "Optimized Hermetic Transform Beam-forming of Acoustic Arrays Via Cascaded Spatial Filter Arrangements Derived Using A Chimerical Evolutionary Genetic Algorithm", Harvey C. Woodsum and Christopher M. Woodsum; International Congress on Acoustics, ICA-13, June 2013—Montreal, Canada, and "Optimization of Cascaded Hermetic Transform Processing Architectures via a Chimerical Hybrid Genetic Algorithm", C. M. Woodsum and H. C. Woodsum, Proceedings of the Sixteenth International Conference on Cognitive and Neural Systems (ICCNS), Boston University, May 30-Jun. 1, 2012, "Beam-forming Devices and Methods", Harvey C. Woodsum; U.S. Pat. No. 8,559,456, Issued Oct. 15, 2013, and "Beam-Forming Devices and Methods", Harvey C. Woodsum, U.S. Pat. No. 8,064,408, Nov. 22, 2009, all of which are incorporated by reference as if fully set forth herein) is $$\underline{H} = \underline{\Sigma}^H \underline{W}$$

Here $\underline{W}$ is a complex matrix obtained by solving the following equation in a least-squares or minimum norm sense (superscript H indicates the hermitian conjugate).

$$\underline{\Sigma}^H \underline{W} \underline{\Sigma} = \underline{I}$$

An example solution is given by the following mathematical expression:

$$\underline{W} = [\underline{\Sigma\Sigma}^H]^\# \underline{\Sigma}(\underline{I}) \underline{\Sigma}^H [\underline{\Sigma\Sigma}^H]^\#$$

For the two-dimensional versions of the transform, a signal manifold is constructed from a set of rectangular matrices that are reshaped to form the columns of the $\underline{\Sigma}$ matrix; these are re-shaped upon reconstruction in the inverse fashion in order to go back to the spatial domain.

Other equivalent methods for obtaining $\underline{H}$ are also described in "Optimized Hermetic Transform Beam-forming of Acoustic Arrays Via Cascaded Spatial Filter Arrangements Derived Using A Chimerical Evolutionary Genetic Algorithm", Harvey C. Woodsum and Christopher M. Woodsum; International Congress on Acoustics, ICA-13, June 2013—Montreal, Canada, and "Optimization of Cascaded Hermetic Transform Processing Architectures via a Chimerical Hybrid Genetic Algorithm", C. M. Woodsum and H. C. Woodsum, Proceedings of the Sixteenth International Conference on Cognitive and Neural Systems (ICCNS), Boston University, May 30-Jun. 1, 2012, "Beamforming Devices and Methods", Harvey C. Woodsum, all of which are incorporated by reference as if fully set forth herein. The Hermetic Transform may optionally include a noise conditioning matrix $\underline{K}$ which normalizes for the effect of white, spatially uncorrelated noise, to the extent that this is present.

$$\underline{H} = \underline{\Sigma}^H \underline{W} \underline{K}$$

The equation for the noise conditioning matrix $\underline{K}$ is as follows:

$$\underline{K} = \underline{R}_{\Sigma\Sigma}[\underline{R}_{NN} + \underline{R}_{\Sigma\Sigma}]^\#$$

where $\underline{R}_{NN}$ is the internal self-noise covariance, and $R_{\Sigma\Sigma}$ is the scaled manifold covariance ($=c\underline{\Sigma\Sigma}^H$ Other forms of tomography are found in the literature, e.g. tomography using ultrasonic radiation. One reference on this subject is the book "Biomedical and Image Processing" by Najarian and Splinter, CRC Press, 2012, which is incorporated by reference as if fully set forth herein. The exemplary embodiments discussed herein are applicable to any of these forms of tomography, and to any imaging system that employs Hermetic Transforms and/or Hermetic Matched Filters in either the signal processing or the tomographic reconstruction algorithm in order to gain resolution.

Additionally, in an exemplary embodiment, for the case of ultrasound, an ultrasonic transducer is used to convert an electrical signal (normally pulsed) into sound at ultrasonic frequencies (frequencies lying above the range of human hearing, therefore above ~20 KHz) through the object, towards an array of receiving transducers which convert the received sound that has passed through the object into an electrical signal (voltage) that can be digitized and processed using algorithms performed by a processor (e.g., computer, microprocessor, or equivalent chip or circuit) in order to create an image. The accumulated attenuation of the signal and/or the time-of-flight (TOF) of the pulsed signal through the object may be used to generate an image. For the case of a TOF system, a Hermetic Matched Filter offers significant time resolution advantages as compared to conventional matched filtering, for a given signal-pulse bandwidth, therefore allowing a much greater precision and accuracy for measurement of time-of-flight through the object. In some cases, for example diffraction tomography, it is advantages to limit the band of the signal via filtering, to frequencies where particular scattering properties are accentuated, e.g. to enhance or inhibit forward scatter modes, or to image particular objects within the larger object via inducement of acoustic resonance. In addition the application of Hermetic Transforms to the beam-forming of the receiving transducer array can allow for more accurate measurement of direct path propagation.

Figure 5:
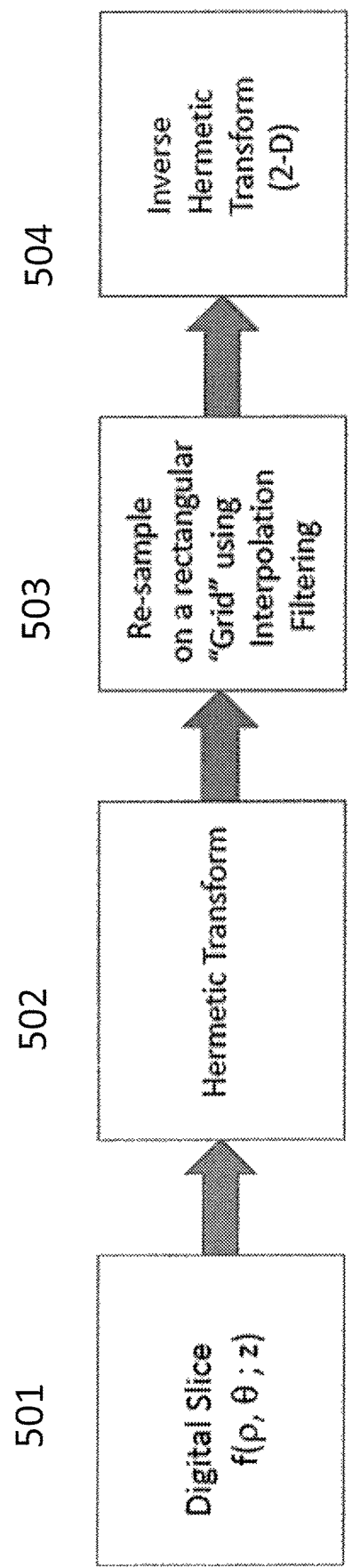
FIG. 5 shows tomographic image construction using a Hermetic Transform according to an exemplary embodiment.

In exemplary embodiments of the disclosed systems and methods, a computer system with a device such as an X-Ray or Radiation Emission CT Scanner, implements a Hermetic Transform version of tomographic reconstruction, as shown in the Block Diagram of FIG. 5. As illustrated in FIG. 5, in an exemplary embodiment, Hermetic Transform Tomography makes use of Hermetic Transforms of a collection of digital slices, each of which is a function of the linear projection dimension ($\rho$) and the rotation angle $\theta$, as well as the position of the slice in the axial dimension (z), as illustrated in 501 and 502. The method re-samples these slices on a uniform grid, and then inverse Hermetic Transforms back to the spatial domain to create a set of volume-image cells ("voxels"), as illustrated in 503 and 504.

Figure 6A:
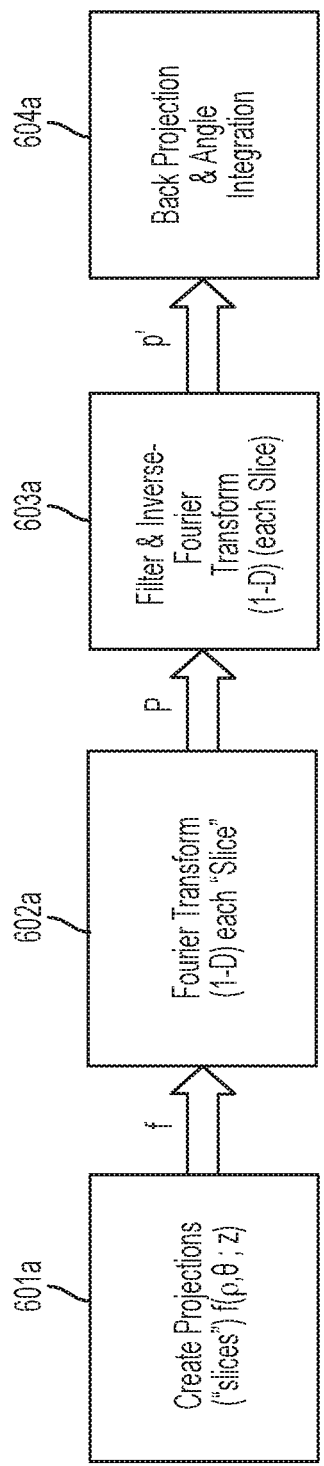
FIGS. 6a and 6b show Filtered Back Projection Tomography using Fourier Transforms and Hermetic Transforms according to exemplary embodiments.
Figure 6B:
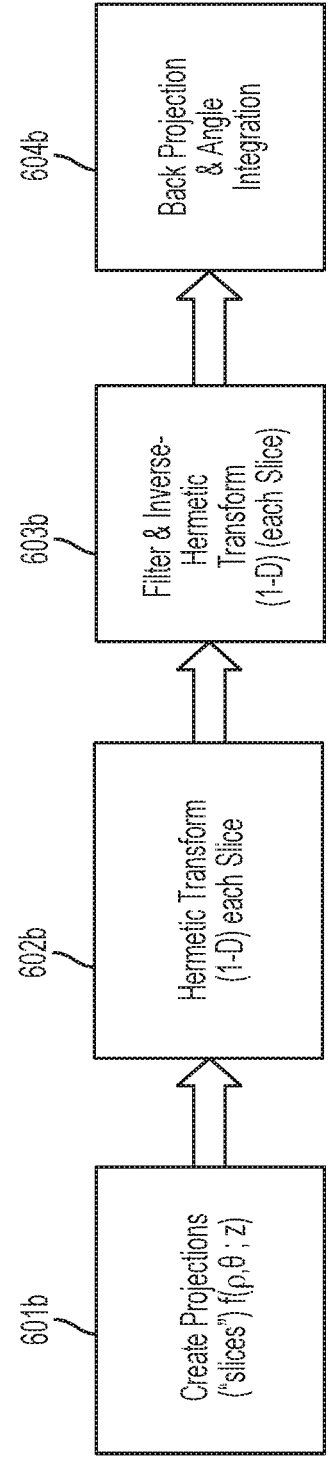

FIGS. 6a and 6b illustrate Filtered Back Projection Tomography using Fourier Transforms and Hermetic Transforms according to exemplary embodiments. In FIG. 6a, Fourier Transform Tomography makes use of Fourier Transforms of a collection of digital slices, each of which is a function of the linear projection dimension ($\rho$) and the rotation angle θ, as well as the position of the slice in the axial dimension (z), as illustrated in 601*a* and 602*a*. The method filters these slides and then inverse Fourier Transforms them back to the spatial domain, as illustrated in 603*a*. Then, a back project and angle integration is performed in 604*a*. In FIG. 6*b*, Hermetic Transform Tomography makes use of Hermetic Transforms of a collection of digital slices, each of which is a function of the linear projection dimension (ρ) and the rotation angle θ, as well as the position of the slice in the axial dimension (z), as illustrated in 601*b* and 602*b*. The method filters these slices and then inverse Hermetic Transforms back to the spatial, as illustrated in 603*b*. Then, a back project and angle integration is performed in 604*b*.

Figure 7:
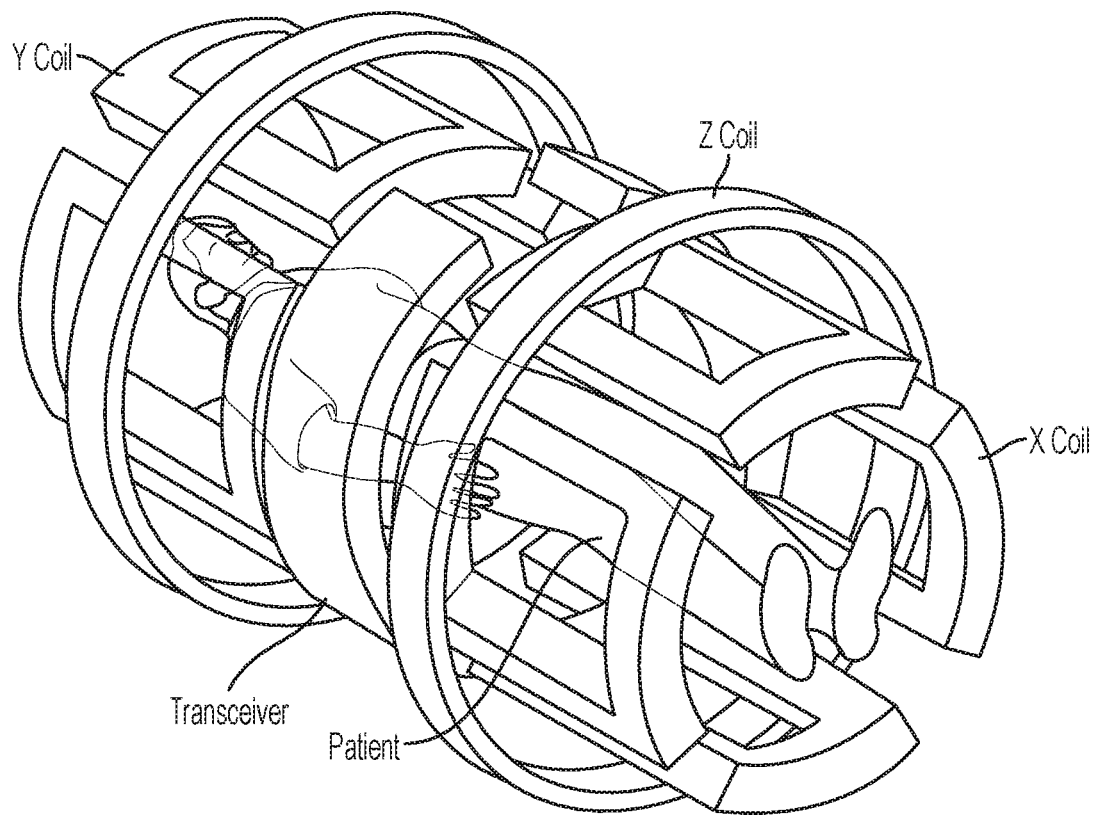
FIG. 7 shows an MRI machine according to an exemplary embodiment.

A major tool in medicine is Magnetic Resonance Imaging (MRI). A graphic depicting an MRI machine according to an exemplary embodiment is illustrated in FIG. 7. Not shown is the signal generation and reception electronics as well as the computers system which processes the data and creates the MRI images. In an exemplary embodiment, an MRI machine such as the one depicted in FIG. 7 can be used with Hermetic Transforms, as discussed further below.

In an MRI machine according to an exemplary embodiment, the effect being harnessed is the alignment of protons in nuclei with an applied magnetic field. A set of perpendicular magnetic fields are applied in orthogonal directions. For example, z in FIG. 7 is along the body axis, while x and y are two axes perpendicular to z and to either other forming a Cartesian coordinate system.

The first principle relating to operation of an MRI is based on the fact that a proton within the magnetic field of the device will tend to align with the field, and will precess about the oriented axis with a frequency proportional to the strength of the field, according to Larmor's formula:

$$\omega_0 \gamma B_0$$

Here $\omega_0$ is the precessional angular frequency (the Larmor frequency), γ is the gyromagnetic ratio in MHz/Tesla, and $B_0$ is the field strength in Tesla. By impressing spatially varying field components (gradients) on the body cavity, the frequency of precession can be made to be position dependent. This means that interactions which depend on precession frequency (or frequency shift) can be made position dependent.

The second principle is based on the fact that a precessing proton can be made to absorb or emit radio-frequency radiation, in order to change the spin orientation. The orientation can range from parallel to the field, to perpendicular to the field, to anti-parallel (opposed to) the field. The lowest energy state is alignment, while the highest energy state is anti-alignment.

In an exemplary embodiment, the body is scanned by transmission and reception of signals that result in state changes for the precessing protons in the nuclei of atoms and molecules. Radio-frequency (RF) energy is transmitted and received through the transceiver portion of the system in the diagram. Proton spins are probed through the application of RF-energy pulse sequences, to measure the response of nuclei along a particular slice, with a particular phase and frequency, in order to then create projection slices as in CT scanning and to measure tissue properties. A series of RF pulses are transmitted to flip spins from lower energy to higher energy states; the nuclei then "relax" back to the lower energy state, releasing RF energy which is received and detected ("echoes"). Slight frequency differences correspond to differing field strengths and, therefore, differing locations within the body.

Within the MRI, the Fourier Transform can be used for image creation from slices (tomography), and also for measurement of frequency in order to identify location of the echo sources (tissues). RF pulse trains are controlled to measure the two different time constants related to decay of the effects of RF relaxation. These are termed T1 and T2. By measuring T1 and T2, information regarding the types of tissue are also obtained. Example tables of T1 and T2 by tissue type are shown in the table in FIG. 8.

Figure 9:
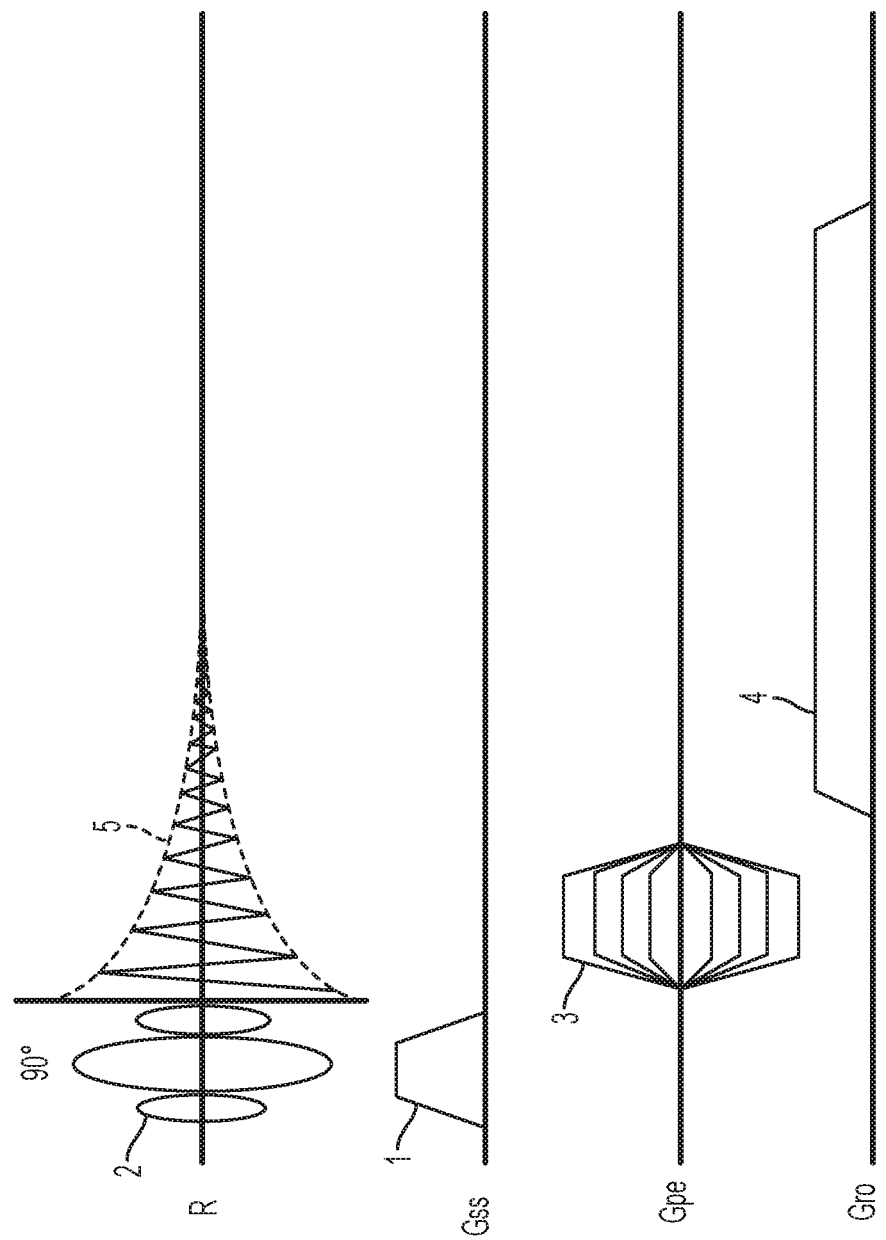
FIG. 9 shows a pulse sequence according to an exemplary embodiment.

FIG. 9 shows a pulse sequence according to an exemplary embodiment. A slice gradient pulse (Gss, 1) is transmitted to select the slice being examined. At the same time a 90 degree RF pulse is transmitted to bias the spin 90 degrees in angle (2); next a phase-encoding pulse (3) is transmitted to set the spin phase, followed by a read-out gradient pulse (Gro, 4). The free-induction decay is measured (5). Example parameters of the device include the pulse repetition time (TR), the echo time (TE), and the flip angle (in this case, 90 degrees). This sequence is merely illustrative, and is not meant to restrict any particular embodiment.

In one or more exemplary embodiments, the ability to precisely measure frequency (hence location) and time properties are affected by the choice of algorithm for processing as well as by the choice of waveform (pulse shape and pulse train design). In particular, the resolution in frequency obtained provides spatial resolution in direct proportion. In addition, motion will cause phase distortion, so being able to measure phase changes allows for motion compensation. Exemplary embodiments of the systems and methods described here create potential performance improvement in several different ways, exploiting the resolution advantage of Hermetic Transforms as follows:

(1) Hermetic Transforms are used in place of Fourier Transforms for tomographic image generation from slices.

(2) Hermetic Transforms are used in place of Fourier Transforms for measuring frequency and thus position of echo sources.

Figure 10:
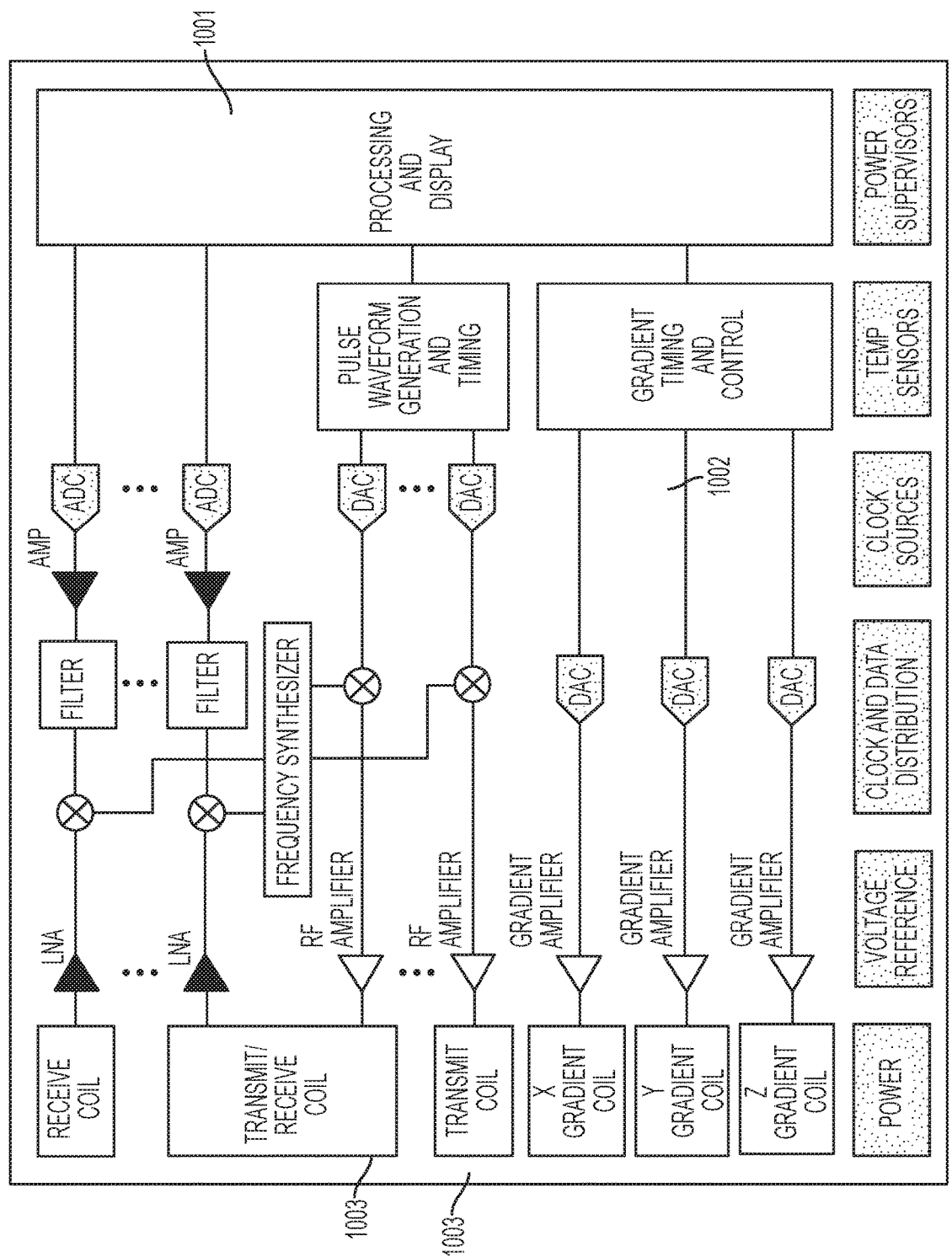
FIG. 10 shows an exemplary hardware oriented diagram for an exemplary MRI embodiment.

An exemplary hardware oriented diagram for an exemplary MRI embodiment is shown in FIG. 10. In the exemplary embodiment shown in FIG. 10, the device as creates three orthogonal magnetic field gradients which are each stimulated by digitally generated signals which are created in a processor 1001 and converted to analog form via digital to analog conversion (DAC's) 1002. Coils 1004 for transmit and receive of radio-frequency signals are used as transducing elements to stimulate the desired nuclear magnetic (or electron-spin magnetic) resonance effects. Because the resonance frequency is a function, generally proportional to the magnetic field strength, particular slices of the object may be interrogated by generating particular pulsed signals and by measurement of signal frequency. In addition, the magnetic resonance may be controlled in such a fashion as to align or de-align the spin phases, and relaxation times of spin resonance decay may be utilized (as described above) to determine material properties. In exemplary embodiments, use of the Hermetic Transform in place of the Fourier Transform within the processor of the system, provides enhanced frequency resolution and therefore, enhanced spatial resolution, typically in the range of 5-10 fold in each dimension. In addition, the coils 1003 within the system may be replaced with a small RF array which can be beam-formed with Hermetic Transforms. The beam-forming aspect can provide better location of resonant RF sources within the object, as well as potential array gain to improve the received pulse signal to noise ratio, both of these advantages resulting in enhanced spatial resolution.

In exemplary embodiments, the systems and methods described here with regards to tomographic reconstruction and other applications can provide benefit in several respects, including the following.

(1) In exemplary embodiments, systems and methods can comprise an enhanced method and process for performing Tomographic Reconstruction of 3-D images using Hermetic Transform in place of Fourier Transforms to process image slices from any type of tomographic data, from any type of radiation, whether from X-Ray, radioactive emission (e.g., Positron Emission sources), sonic or ultrasonic, etc., as well as Magnetic Resonance Imaging, Nuclear Quadropole Imaging, and Electron Paramagnetic Imaging, such method and process replacing Fourier Transform based reconstruction with Hermetic Transform based reconstruction.

(2) In exemplary embodiments, these benefits can accrue for devices which employ the method and process of (1) in order to accomplish useful imaging of objects animate or inanimate, including applications to medicine and non-destructive testing or examination of said objects.

(3) In exemplary embodiments, these benefits can also accrue for devices employing the methods and process of (1) in order to accomplish probing of various aspects of the environment, e.g., the electron density of the ionosphere, seismic parameters of the earth, and sound velocity and/or temperature profiles of the ocean.

In exemplary embodiments, systems and methods for MRI, other related imaging modalities, and other applications can also include the following benefits.

(1) In exemplary embodiments, use of Hermetic Transforms allows more precise correlation (e.g., Hermetic Matched-Filtering) involving more accurate location of spin-echoes in time. Hermetic Matched Filtering in exemplary embodiments also permits shorter observation intervals so that phases can be more accurately tracked to allow motion compensation in "fast" MRI system.

(2) In exemplary embodiments, use of Hermetic Transforms for beam-forming of RF "pickup" arrays in an MRI system, which can be substantially smaller than a wave-length, improves signal to noise ratio of the device as well further improves spatial resolution of the device.

(3) In exemplary embodiments, image resolution depends on field gradient, so increased resolution can be traded off against field strength (i.e., smaller magnets could be used while retaining the resolution of current MRI type devices). Additionally, lower magnetic field strengths may provide more resolution per field strength due to physical effects which have been classically been found to be less important than field strength in tradeoff studies.

In further exemplary embodiments, the above advantages also apply to other forms of Magnetic Resonance, such as Electron Paramagnetic Resonance (EPRI) and Nuclear Quadrapole resonance (NQPRI).

Additionally, in further exemplary embodiments a magnetic resonance imaging device comprising a means of creating and changing orthogonal magnetic field components, as well as transmitting and receiving radio-frequency energy, making use of magnetic resonance physics in order to image particular types of tissues. Additionally, Resonance Imaging Devices and Processing Methods, can include MRI, EPRI, NQRI, etc., which make use of Hermetic Transforms for frequency, time, and spatial measurements. Resonance Imaging Devices can also make use of Hermetic Transforms in Tomographic image formation and analysis. Furthermore, the above exemplary devices can be applied to human and animal medical purposes as well as to magnetic resonance microscopy.

Figure 11:
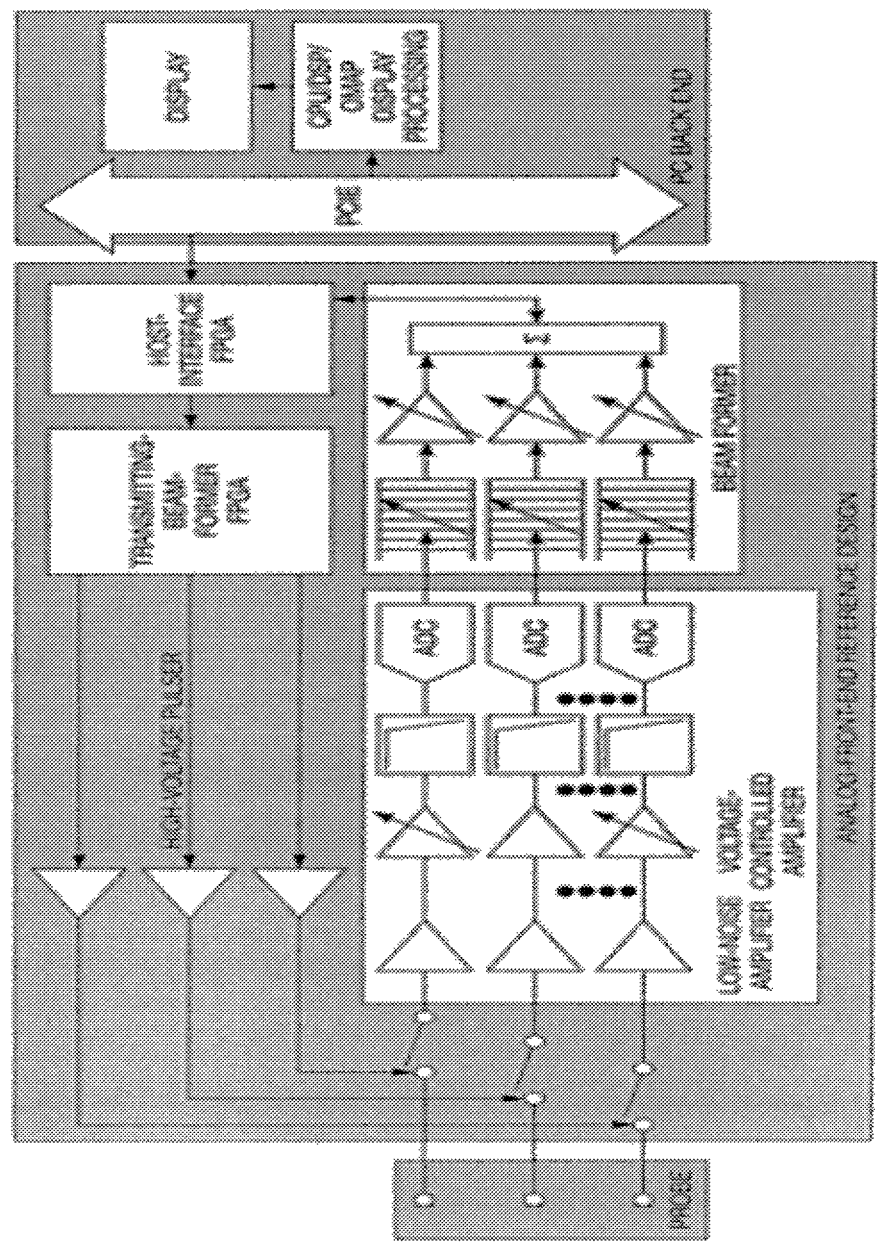
FIG. 11 shows a block diagram of an ultrasonic imaging device according to an exemplary embodiment.

A major tool of modern medicine is ultrasonic imaging, which is primarily utilized as means of gaining information for diagnostic purposes. Ultrasound devices are also used for therapeutic purposes other than imaging, such as in lithotripsy and low-intensity pulsed ultrasound (LIPUS). A block diagram of an ultrasonic imaging device according to an exemplary embodiment is shown in FIG. 11.

In an exemplary embodiment, an ultrasonic transducer, which can be an array of transducing elements, creates sound at frequencies above the range of human hearing (>20 KHz) in response to electrical signals which are fed to the various array elements. The elements may operate on the principle of the piezoelectric effect. Sound generated by such means can be beam-formed to create plane or focused waves. Propagation of the sound within the body is affected by acoustic index of refraction, and acoustic impedance, to include sound absorption properties. A means of application for such a device in a medical context is echo-ranging, analogous to echo-ranging in sonar or radar. The transmitting array is coupled to the human body, for example, with an impedance-matching gel place on the skin. Ultrasonic sound waves are transmitted into the body, and as they propagate and encounter tissues of varying acoustic impedance, some of the sound is reflected back towards the array, where the reflected sound waves are beam-formed to create an image of the tissues and organs within the body. Time delay of propagation, when combined with the speed of sound, gives a measure of distance along the path of propagation, while angles of returning echoes are resolved via beam-forming to create the other two dimensions of the image. Moving objects, e.g., a beating heart, can be observed specially via measurement of frequency shifts proportional to the velocity of motion (due to the Doppler Effect).

In an exemplary embodiment, an ultrasound device utilizes digital signal processing for beam-forming (transmit and/or receive) as well as for frequency spectrum analysis for Doppler Frequency Measurement. Special pulses and pulse trains may be employed to optimize the measurement process. Hermetic Transforms, when utilized in digital signal processing, can provide performance advantages in terms of space, time, and frequency resolution.

In addition, in an exemplary embodiment, placement of the ultrasonic receiving array allows tomographic image reconstruction from either sound attenuation measurements or time of flight sound measurements, or both.

Accordingly, one or more exemplary embodiments can include a device with one or more of the following features. The device can comprise a means of signal generation and transmit beam-forming (an ultrasonic transmitting array and beam-former), with a means of receiving ultrasonic echoes from tissues within the body (an ultrasonic receiving array), a means of digitally acquiring and beam-forming echoes received by system, with either the transmitting and/or receive beam-forming system making use of Hermetic Transforms in order to gain resolution advantage. The device can be for making use of Hermetic Matched Filtering in order to gain resolution in time and therefore propagation delay measurement. The device can be used for making use of Hermetic Transforms for frequency analysis in order to improve Doppler frequency shift measurement resolution. The device of can be in a bi-static or multi-static geometry (e.g., transmitting and receiving array not co-located). The device can be in a tomographic application either through absorption or diffraction. The device can include the addition of contrast agents. The device of can be used in a therapeutic application, whether for tissue heating, ultrasonic neuromodulation, lithotripsy, or for low-intensity pulsed ultrasound. The device can be used with filtering of the transmitted pulsed signals in order to enhance specific resonance modes to enhance image resolution of particular object characteristics. The device can be used in medical and/or non-medical applications.

Figure 12A:
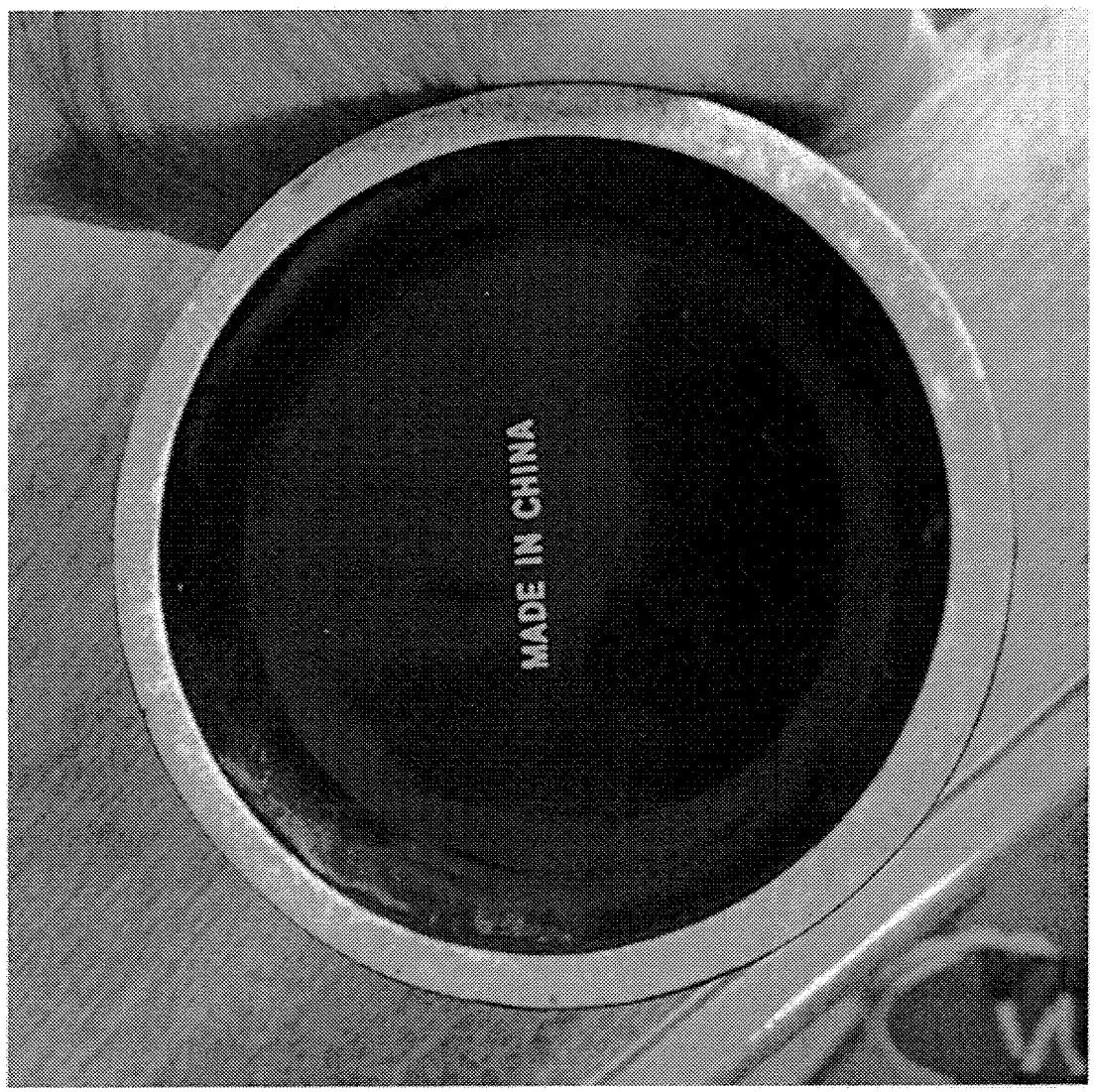
FIGS. 12a through 12c shows a comparison of the image object (FIG. 12a), a Fourier Reconstruction with 4× oversampling (FIG. 12b), and a Hermetic Transform Reconstruction with 4× oversampling (FIG. 12c) produced using an exemplary test-setup.
Figure 12B:
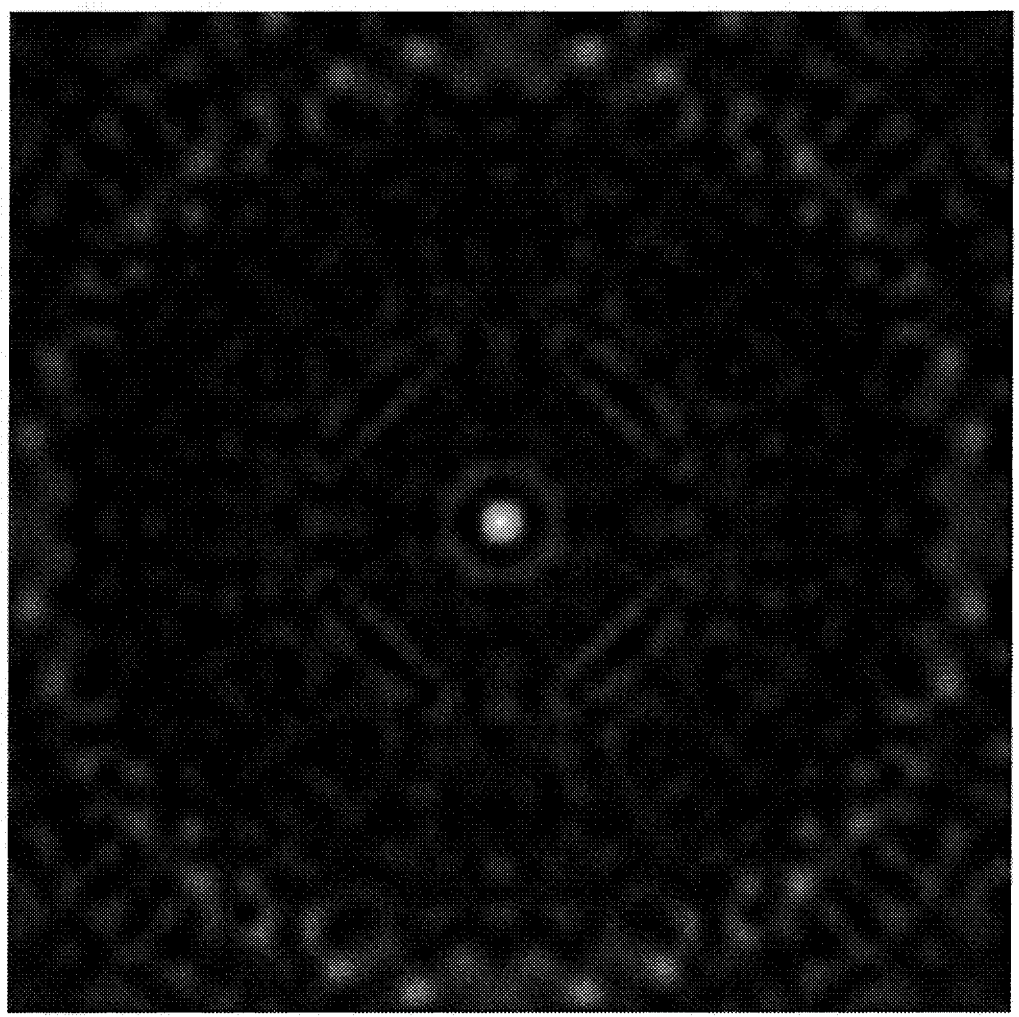
Figure 12C:
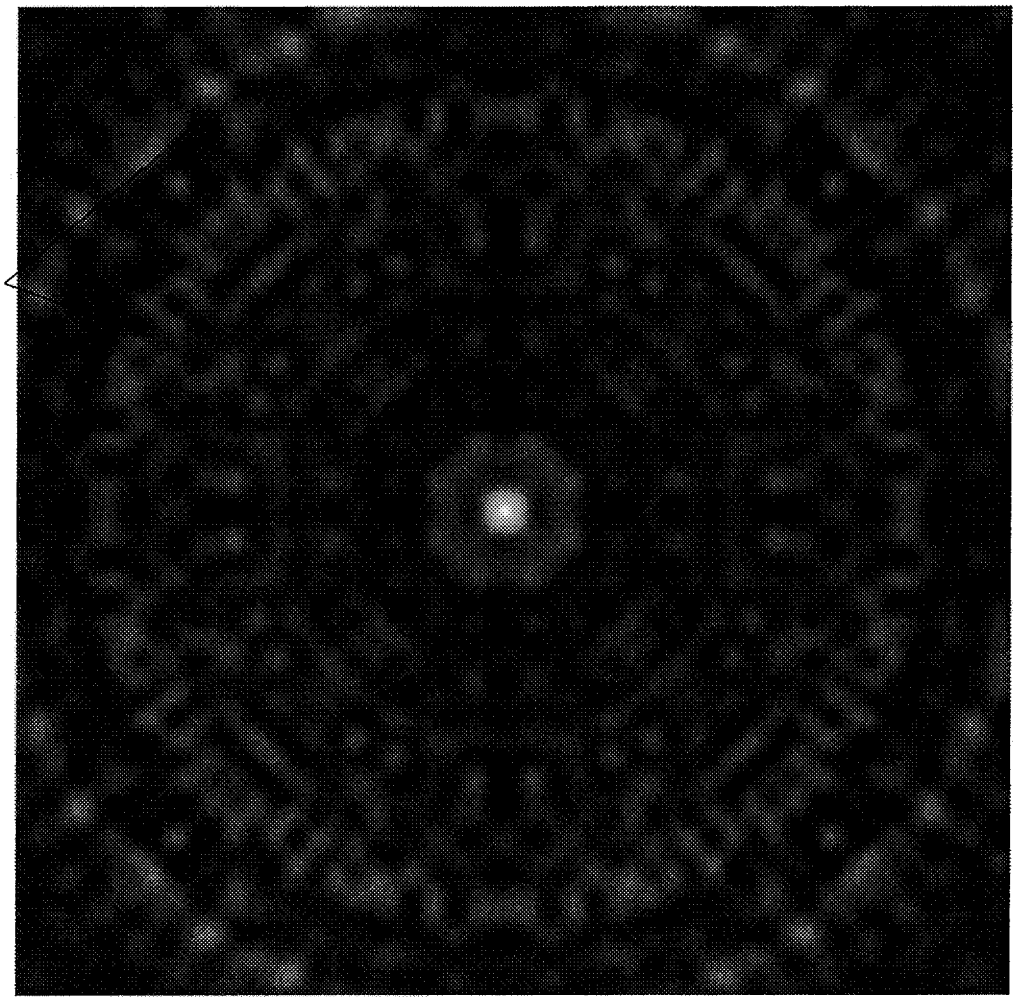

In an exemplary acoustic tomography embodiment, it has been shown experimentally that Hermetic Transform tomography can provide performance benefits relative to tomography using a Fourier Transform. An exemplary test-setup comprises an object (e.g., a cup), a microphone with adjustable locations, a rotatable platform for moving the object, and a transmitting transducer (e.g., a loud speaker). The exemplary test-setup employed 4 KHz to 16 KHz pulses with 44,100 Hz sampling for testing, although it will be appreciated that other frequencies and sampling rates can be employed. In the exemplary test-setup, the loud speaker transmitted at the object with the scattered sound being picked up by the microphone that could be moved to a number of positions laterally. In the exemplary test-setup, 10 positions and 36 slices were used, created by rotating the object, although it will be appreciated that other numbers of positions and slices could also be used. Peak sound intensity at each position was used to create the slices. FIG. 12 shows a comparison of the image object (FIG. 12a), a Fourier Reconstruction with 4× oversampling (FIG. 12b), and a Hermetic Transform Reconstruction with 4× oversampling (FIG. 12c) produced using an exemplary test-setup. As shown in the figures, the Hermetic Transform Reconstruction resulted in more resolution, accuracy, and preservation of important features, such as the outer and inner walls.

In one or more exemplary embodiments, robust Hermetic Transforms can be used to address robust variations in noise as well as to other signal amplitude and phase fluctuations, in order to create a robust transform. Such a transform can have the advantages for measurement of signal parameters such as signal location in frequency, space, and in time, as well as to detect and measure and phase variations and decay time. Imaging devices can employ this method in the measurement of signal parameters, including signal location in frequency, space, and time, as well as for tracking of phase variations and decay time.

In particular, taking as an example, the frequency measurement problem in an MRI machine, it desirable to create a Hermetic Transform that is robust to any variations that might be observed, such as noise, random variations in signal phase or amplitude, etc. A method of incorporating these types of variations is to develop a modified equation for the Hermetic Transform which optimizes performance over the anticipated range of variation. As an example we take the case of a known signal set (e.g. a matrix of complex sinusoids), which we will call $\underline{\Sigma}$, where each column of the matrix is comprised of a samples of a complex sinusoid of frequency ωk, that may be observed in presence of some perturbing noise (represented by a vector of noise samples $\underline{N}$). We can define an equation that will define the Hermetic Transform for this case.

We start with the canonical equation for Hermetic Transforms, $$\underline{H}^o\underline{\Sigma}=\underline{I}$$

We desire additionally that the Hermetic Transform satisfy the following equation, $$\underline{HN}=\underline{0}$$

i.e. that the Hermetic Transform is orthogonal to the noise.

In a practical sense we can use multiple noisy references or create them from multiple noise realizations. As such, we can construct the following equation:

$$\underline{H}[(\underline{\Sigma}+\underline{N}_1)(\underline{\Sigma}+\underline{N}_2)\ldots]=[\underline{II}\ldots]=\underline{\rho}$$

Thus, we can develop an equation that can be solved for a Hermetic Transform which creates the desired properties.

Defining matrices $\underline{\sigma}$ and $\underline{\Omega}$ with the following equations, $$\underline{\sigma}=[(\underline{\Sigma}+\underline{N}_1)(\underline{\Sigma}+\underline{N}_2)\ldots]$$

$$\underline{H}=\underline{\Sigma}^K\underline{\Omega}$$

the equation to be solved for the noise conditioned DHT in terms of these variables is $$\Sigma^H\underline{\Omega}\underline{\sigma}=\underline{\rho}$$

The matrix $\underline{\Omega}$ (and therefore $\underline{H}$) can be solved for using standard linear algebra via multiplying by pseudo-inverse matrices derived from the well-known Moore-Penrose Singular Value Decomposition (SVD), $$\underline{\Omega}=pinv(\underline{\Sigma}^H)\rho\, pinv(\sigma)$$

Here pinv( ) is the pseudo-inverse operation.

Other types of variability, such as random amplitude and phase variations introduced by post multiplying $\Sigma$ by a diagonal matrix L of such variations in order to create the following equation:

$$H[(\Sigma\Lambda_1+N_1)(\Sigma\Lambda_2+N_2)\ldots]=[\Lambda_1\Lambda_2\ldots]$$

Here the matrices are diagonal matrices with random diagonal elements having random amplitude and phase variations. The above equation can be solved by setting H=$\Sigma^H\Omega$ and applying the pseudo-inverses of the appropriate matrices as above. This approach is not meant to preclude any other similar form of training for variation.

In one or more further exemplary embodiments, an imaging device, having an RF array or acoustic array as part of the scanning apparatus, first applies Hermetic Matched Filtering to each antenna or transducer channel, and then creates beams for additional spatial filtering and signal separation, via a time-delay, time-domain beamforming approach, whether in a computer system or other digital processor or in multiple processors or in an equivalent circuit that performs the same function.

In an exemplary embodiment, an alternate use of Hermetic Matched Filtering beyond the use of signal location in time is in analogy to replica correlation, wherein the a antenna channels in the RF pickup array are processed with Hermetic Matched Filter, matched to a nominal signal replica, and then beamformed in the time domain (for related background, see Woodsum, in U.S. Patent Application 20150145716, "Radar Using Hermetic Transforms," which is hereby incorporated by reference herein in its entirety). An exemplary embodiment can be implemented using a single row of the Hermetic Transform matched filter matrix utilized to process each antenna channel. In terms of implementation, one embodiment is to first select one row of the Hermetic Matched Filter to make a Hermetic Vector and convolve this vector with a sliding Spectral Transform (Fourier or Hermetic) of each channel data stream. As an example, a sliding DFT algorithm can be utilized for short-term Fourier/Hermetic Transform. Multiple Hermetic Matched Filters can also be applied in parallel, one for each frequency cell, creating multiple frequency-filtered streams for each element. The channels corresponding to a particular Hermetic Matched Replica are then combined using beamforming, for example, a time delay beam-former. Each channel is weighted (e.g., with a Hanning Function) and time-delayed according to a time-delay table, prior to summation to form a beam. There is one set of weights and delays for each beam to be formed. The angular resolution is directly proportional to the array dimension and inversely proportional to the time resolution of the compressed (matched filtered) waveform as measured at the output of the Hermetic Matched Filter stage. For example, an 8:1 reduction in echo peak duration will produce an 8:1 radian angle resolution improvement, although other reductions and improvements are possible.

In one or more further exemplary embodiments, devices and methods obtain signal decay constants using Hermetic Transforms derived from a manifold of signals having complex frequency, or otherwise representing various signal decay characteristics, in order to determine decay parameters of processed signals, whether processed by a computer system, other digital processor, or circuit performing the equivalent function.

In an exemplary embodiment, Hermetic Transforms can be derived from complex sinusoids used to measure frequency, while magnetic imaging systems (e.g. MRI) also requirement measurement of decay constants (T1, T2) of damped sinuosoids as an aid in determining tissue composition, as well as frequency, used to determine tissue location. Hermetic Transforms can be extended by treating the decaying sinusoid as having complex frequency, and using a basis set $\underline{\Sigma}$ that is formed from such functions. Numerical simulations of an exemplary embodiment illustrate that superior results can be obtained in the determination of decay time constants as compared to Fourier Transforms. Results of numerical simulations for an exemplary embodiment are present here for illustration in FIGS. 13a through 13e, though it would be understood that other results could also be obtained.

A discrete-time signal manifold consisting of complex sinusoids of the same frequency (1/20 of the sampling frequency) with monotonically and logarithmically increasing damping constants (imaginary part of frequency) (ranging from 1/20 of the sampling frequency to 1/10 of the sampling frequency) was created with the Hermetically orthogonal basis of five (5) such signals. To test decay constant estimation, a set of 100 signals having random phases and random damping (within the manifold damping band) was generated.

To create the Fourier baseline, the line width of the Fourier Spectral Density curve was obtained and used to calculate estimated values of the damping constant for each test sample, according to the standard relation $\kappa = pi \cdot \delta$, where $\delta$ is the line width and $\kappa$ is the damping constant from a function of the form $y(t) = \exp((2 \cdot pi \cdot f + i \cdot \kappa) \cdot i \cdot t)$, and where f is the signal frequency.

Hermetic estimation of damping was executed by performing a Hermetic Transform of the test samples to generate a vector of signal similarity to each basis function. Hermetic power spectral density or HPSD (the Hermetic analog of the Periodogram) was created from the absolute value squared of the Hermetic Transform of the signal, and normalized to a probability distribution and the expectation damping constant was determined. Results from these simulations show that exemplary embodiments of the Hermetic Damping Filter method generally exceeded the Fourier filtering method by a wide margin and did not perform significantly worse on any samples.

Figure 13A:
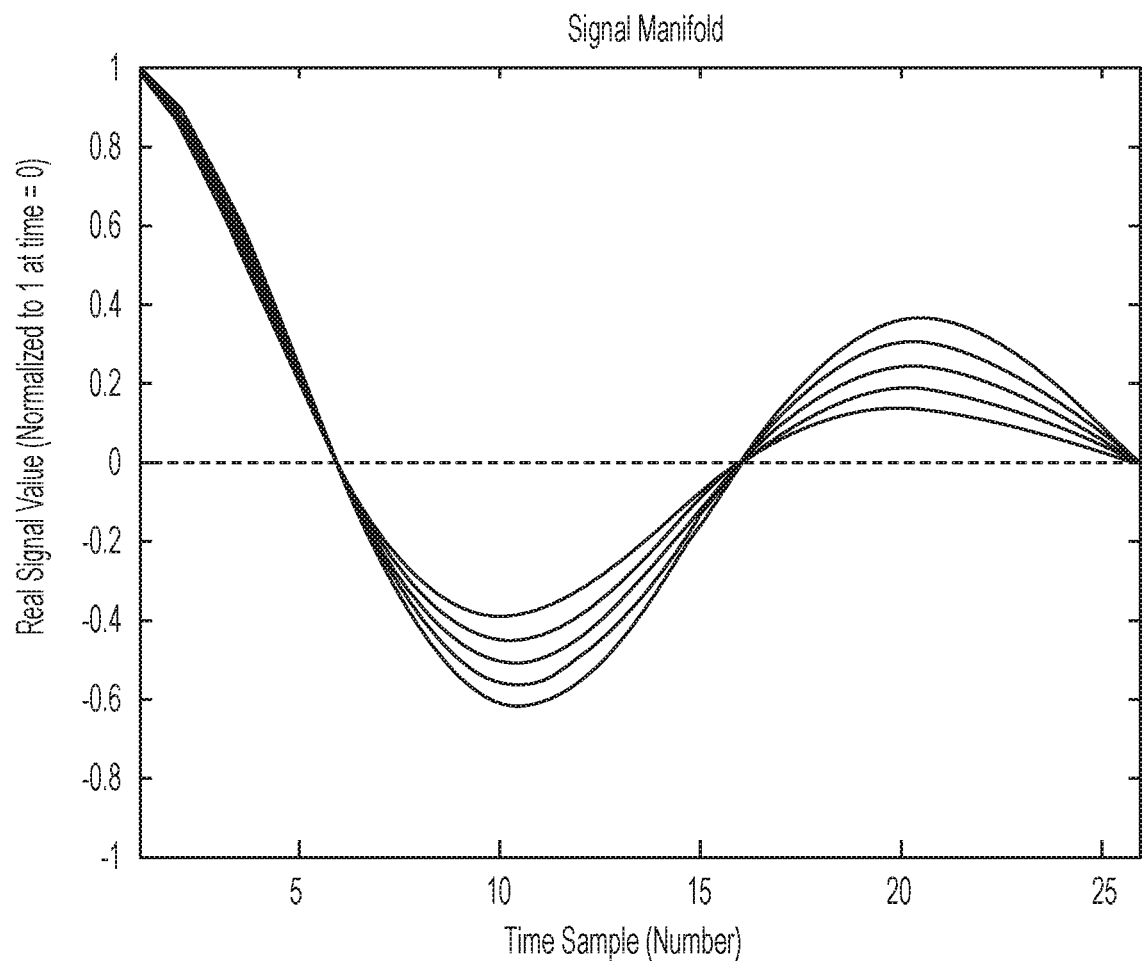
FIGS. 13a through 13e show results of numerical simulations for an exemplary embodiment.

FIG. 13a shows the real part of the 5 basis functions utilized to make a Hermetic Transform for measuring the decay constant. The manifold matrix is comprised of the basis functions arranged as column vectors. These functions are shown to be orthogonal according to the quadradic form below:

$$\underline{\Sigma}^H \underline{W} \underline{\Sigma} = \underline{I}$$

Figure 13B:
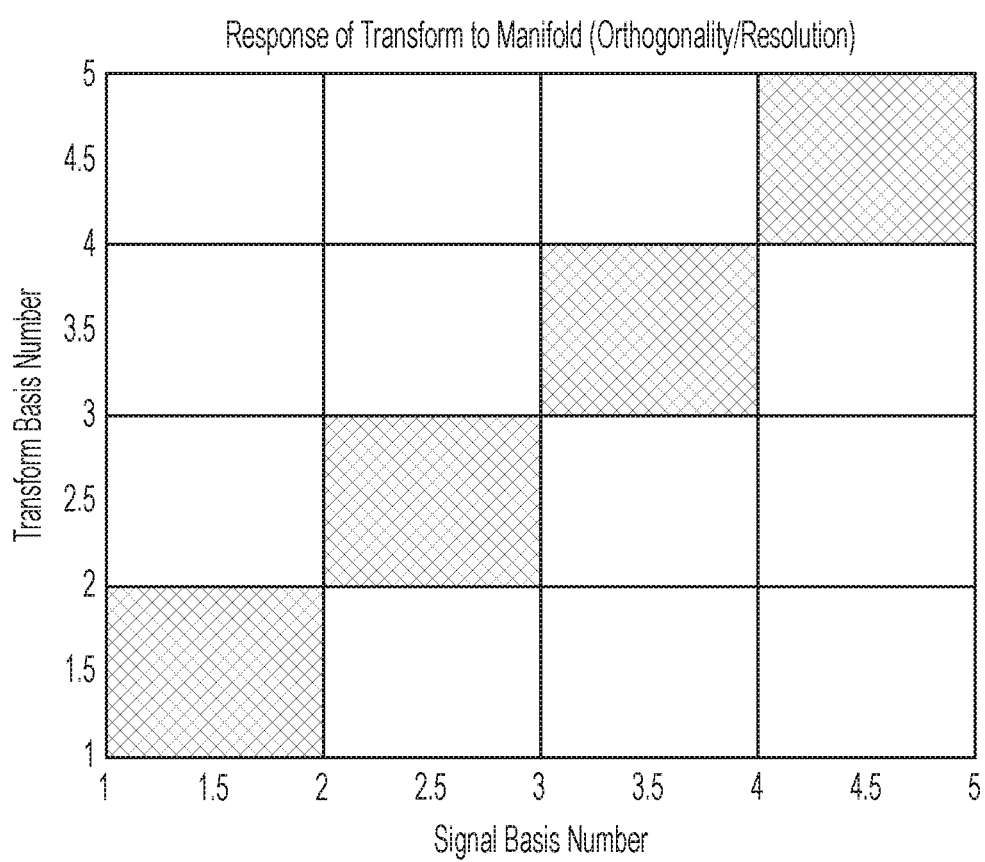
Figure 13C:
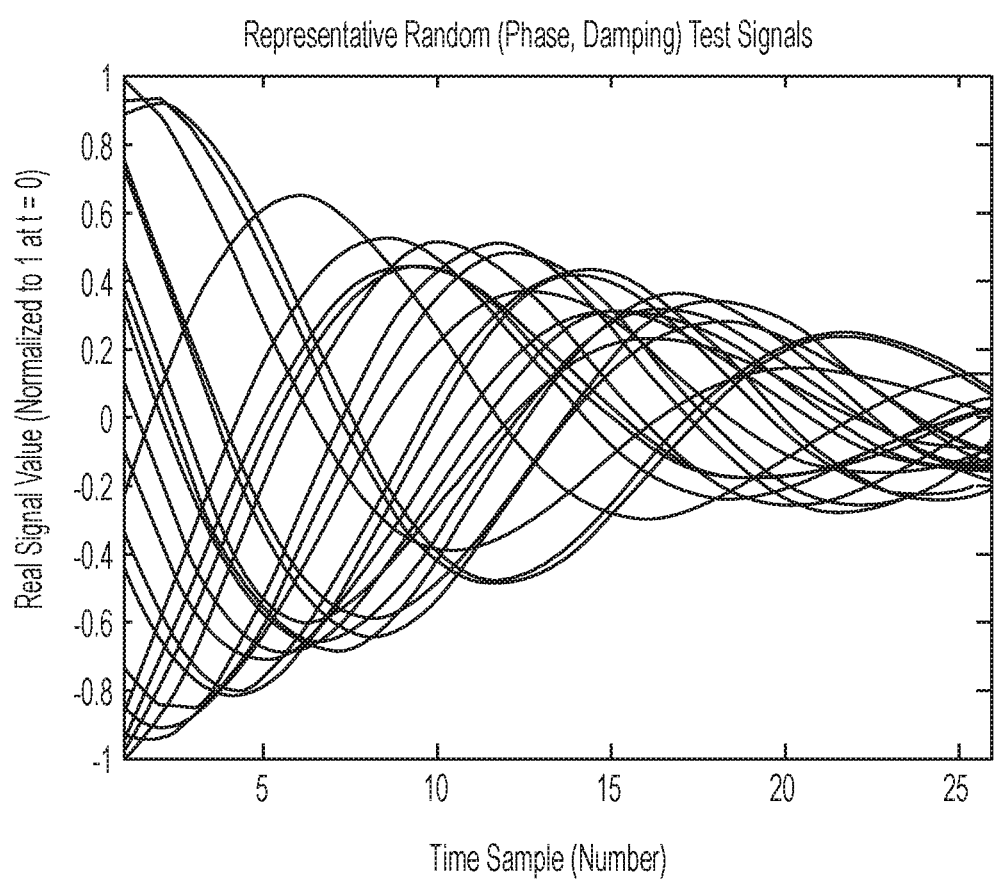
Figure 13D:
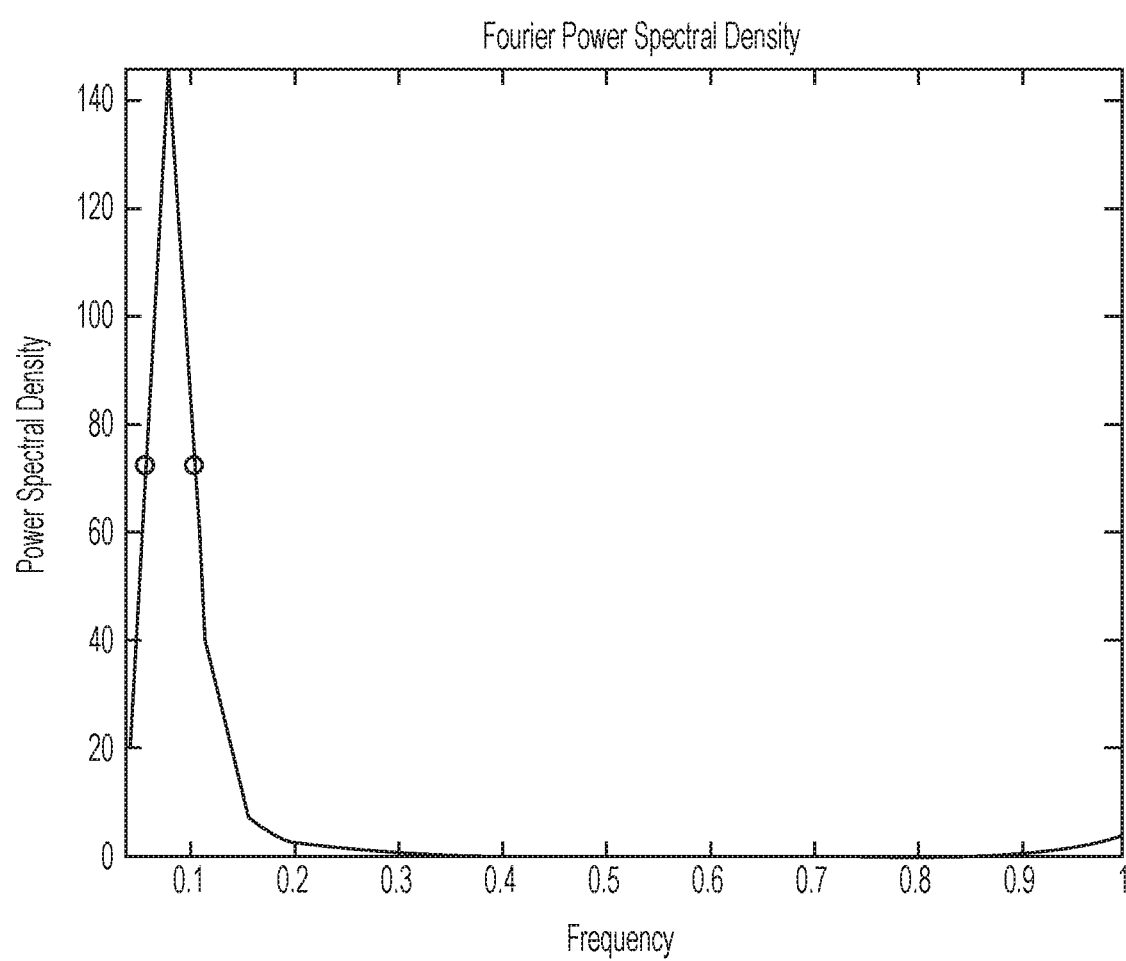
Figure 13E:
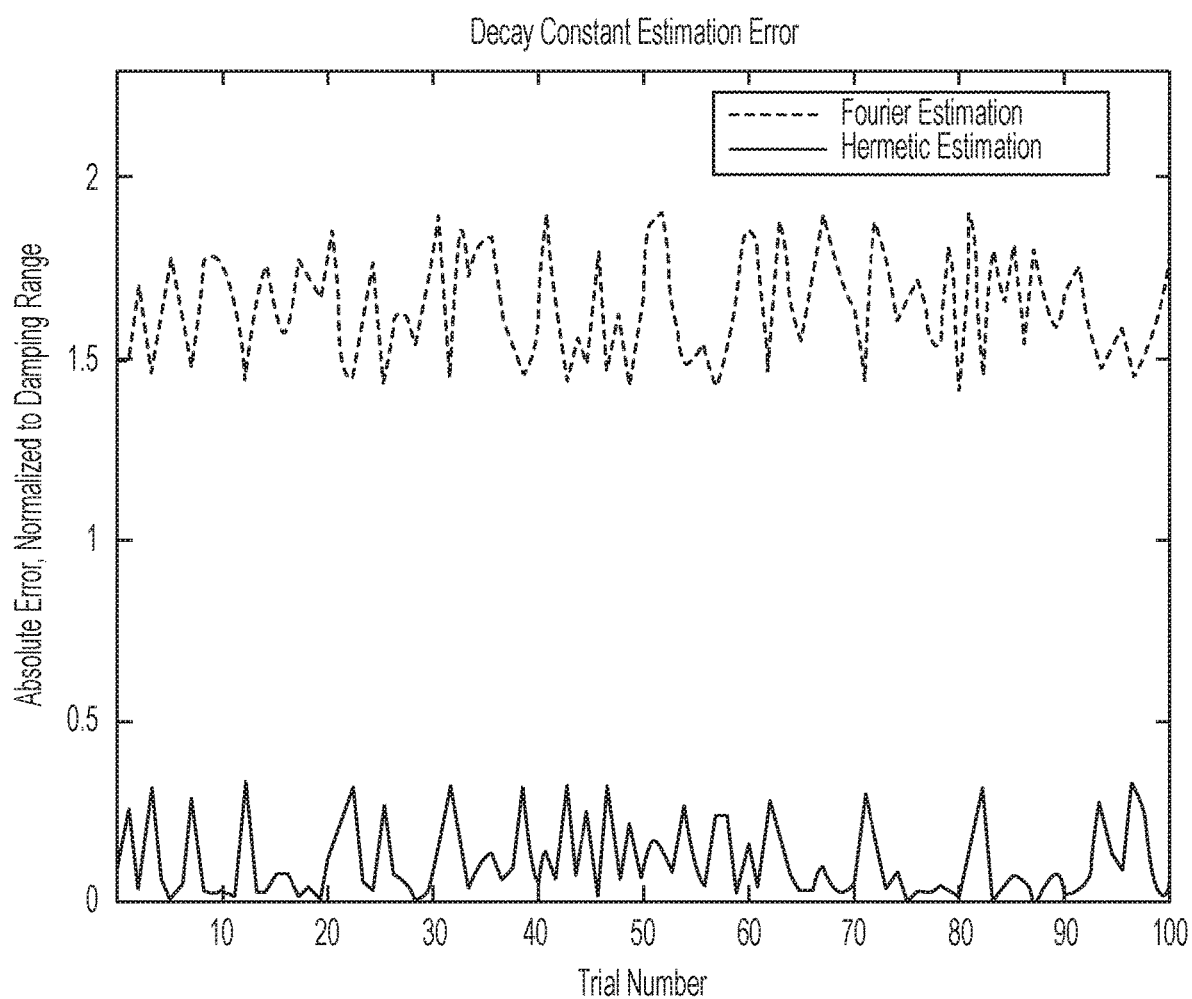

Here $\underline{\Sigma}$ is the manifold matrix, $\underline{W}$ is the weight matrix corresponding to a metric for the complex non-Euclidean signal space, and $\underline{I}$ is the identity matrix. The Hermetic Transform is $\underline{H} = \underline{\Sigma}^H \underline{W}$ This equation matches the standard definition of the Hermetic Transform, however the manifold is comprised of complex sinusoids having complex frequency. FIG. 13b shows that the identity matrix indicates the desired diagonal checkerboard pattern of the response of the transform to the basis set. FIG. 13c indicates a set of test signals (real part) with varying amplitudes, phases, and decay constants (all with the same real part of frequency). FIG. 13d indicates the FFT derived power spectrum of a representative test signal, with the half-power points marked on the curve to show the frequency bandwidth derived from this spectrum and used in the standard method in order to estimate the decay constant of the signal. FIG. 13e shows the comparative error from an ensemble of 100 such signals, with an exemplary embodiment of the Hermetic Transform method resulting in a much lower error of decay parameter estimation.

It will be appreciated that while a particular sequence of steps has been shown and described for purposes of explanation, the sequence may be varied in certain respects, or the steps may be combined, while still obtaining the desired configuration. Additionally, modifications to the disclosed embodiments and the invention as claimed are possible and within the scope of this disclosed invention.

The invention claimed is:

1. A tomography device comprising:
   a scanner that obtains at least one image slice of an object, the at least one image slice comprising oversampled image data; and
   at least one processor configured to:
   perform Hermetic Transform Tomography comprising calculating a robust Hermetic Transform on the at least one image slice to obtain hermetically transformed data, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \quad \text{(a)}$$

$$\underline{H} = \underline{\Sigma}^K \underline{\Omega}; \text{ and} \quad \text{(b)}$$

$$\underline{\sigma} = [(\underline{\Sigma} + \underline{N}_1)(\underline{\Sigma} + \underline{N}_2) \ldots ]; \quad \text{(c)}$$

filter and perform an inverse operation comprising a pseudo-inverse of a robust Inverse Hermetic Transform using the Moore-Penrose Pseudo-Inverse performed with a Singular Value Decomposition on the Hermetic Transform data to obtain filtered inverse Hermetic Transform data; and
   perform back projection and angle integration on the filtered inverse Hermetic Transform data to produce a three-dimensional image of the object.

2. The device of claim 1, wherein the scanner obtains the at least one image slice through at least one of X-Ray imaging, radioactive emission imaging, Positron Emission imaging, sonic imaging, ultrasonic imaging, Magnetic Resonance Imaging, Nuclear Quadropole Imaging, or Electron Paramagnetic Imaging.

3. The device of claim 1, wherein the scanner obtains the at least one image slice through at least one of measuring attenuation of radiation, measuring time of flight radiation, or measuring forward scatter diffraction.

4. The device of claim 1, wherein the robust Hermetic Transform is orthogonal in a minimum-norm or a least-squares sense to a vector of noise samples.

5. The device of claim 1, wherein the robust Hermetic Transform is determined based on a plurality of noisy references.

6. A method of obtaining a tomographic image comprising:
  obtaining at least one image slice of an object, the at least one image slice comprising oversampled image data;
  performing Hermetic Transform Tomography comprising calculating a robust Hermetic Transform on the at least one image slice to obtain hermetically transformed data, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \quad (a)$$

$$\underline{H} = \underline{\Sigma}^K \underline{\Omega}; \text{ and} \quad (b)$$

$$\underline{\sigma} = [(\underline{\Sigma} + \underline{N}_1)(\underline{\Sigma} + \underline{N}_2) \ldots ]; \quad (c)$$

filtering and performing an inverse operation comprising a pseudo-inverse of a robust Inverse Hermetic Transform using the Moore-Penrose Pseudo-Inverse performed with a Singular Value Decomposition on the Hermetic Transform data to obtain filtered inverse Hermetic Transform data; and
  performing back projection and angle integration on the filtered inverse Hermetic Transform data to produce a three-dimensional image of the object.

7. The method of claim 6, wherein obtaining the at least one image slice comprises using at least one of X-Ray imaging, radioactive emission imaging, Positron Emission imaging, sonic imaging, ultrasonic imaging, Magnetic Resonance Imaging, Nuclear Quadropole Imaging, or Electron Paramagnetic Imaging.

8. The method of claim 6, wherein obtaining the at least one image slice comprises at least one of measuring attenuation of radiation, measuring time of flight radiation, or measuring forward scatter diffraction.

9. A measuring device comprising:
  a scanner that obtains at least one signal parameter, the at least one signal parameter comprising oversampled signal data; and
  at least one processor configured to perform a robust Hermetic Transform on the at least one signal parameter to obtain a measurement associated with the signal parameter, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \quad (a)$$

$$\underline{H} = \underline{\Sigma}^K \underline{\Omega}; \text{ and} \quad (b)$$

$$\underline{\sigma} = [(\underline{\Sigma} + \underline{N}_1)(\underline{\Sigma} + \underline{N}_2) \ldots ]. \quad (c)$$

10. The device of claim 9, wherein
  the at least one signal parameter comprises frequency data; and
  the at least one processor is further configured to determine a position of an object using the robust Hermetic Transform of the signal parameters.

11. The device of claim 9, wherein
  the at least one signal parameter comprises time data; and
  the at least one processor is further configured to perform Hermetic Matched Filtering to locate echoes.

12. The device of claim 9, wherein the at least one processor is further configured to perform motion compensation by tracking phases using the robust Hermetic Transform of the signal parameters.

13. The device of claim 9, wherein
  the at least one signal parameter comprises spatial data;
  the scanner further comprises an RF array; and
  the at least one processor is further configured to perform Hermetic Transform antenna beam forming on the RF array.

14. The device of claim 9, wherein obtaining the at least one signal parameter using scanner comprises at least one of Magnetic Resonance Imaging (MIR), Electron Paramagnetic Resonance (EPRI), or Nuclear Quadrapole resonance (NQPRI).

15. The device of claim 9, wherein the at least one signal parameter comprise at least one of signal location in frequency, signal location in space, signal location in time, tracking of phase variations, or tracking of decay time.

16. The device of claim 9, wherein:
  the at least one signal parameter comprises a complex frequency comprising a real frequency part and an imaginary frequency part, the imaginary frequency part corresponding to a signal decay constant; and
  the at least one processor is further configured to obtain signal decay constants using the robust Hermetic Transform to determine a material composition of the object from the signal decay constants.

17. A method of measuring signal parameters comprising:
  obtaining at least one signal parameter, the at least one signal parameter comprising oversampled signal data; and
  performing a robust Hermetic Transform on the at least one signal parameter to obtain a measurement associated with the signal parameter, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \quad (a)$$

$$\underline{H} = \underline{\Sigma}^K \underline{\Omega}; \text{ and} \quad (b)$$

$$\underline{\sigma} = [(\underline{\Sigma} + \underline{N}_1)(\underline{\Sigma} + \underline{N}_2) \ldots ]. \quad (c)$$

18. The method of claim 17, wherein
  the at least one signal parameter comprises frequency data; and
  performing the robust Hermetic Transform on the at least one signal parameter comprises determining a position of an object.

19. The method of claim 17, wherein
  the at least one signal parameter comprises time data; and
  performing the robust Hermetic Transform on the at least one signal parameter comprises performing Hermetic Matched Filtering to locate echoes.

20. The method of claim 17, further comprising tracking phases to perform motion compensation.

21. The method of claim 17, wherein
the at least one signal parameter comprises spatial data; and
performing the robust Hermetic Transform on the at least one signal parameters comprises beam forming an RF array.

22. The method of claim 17, wherein obtaining the at least one signal parameter comprises at least one of Magnetic Resonance Imaging (MIR), Electron Paramagnetic Resonance (EPRI), or Nuclear Quadrapole resonance (NQPRI).

23. The method of claim 17, wherein the at least one signal parameter comprise at least one of signal location in frequency, signal location in space, signal location in time, tracking of phase variations, or tracking of decay time.

24. The method of claim 17, wherein:
the at least one signal parameter comprises a complex frequency comprising a real frequency part and an imaginary frequency part, the imaginary frequency part corresponding to a signal decay constant; and
performing the robust Hermetic Transform on the at least one signal parameter comprises obtaining signal decay constants to determine a material composition of the object from the signal decay constants, wherein the robust Hermetic Transform is generated using a basis set comprised on exponentially decaying complex sinusoidal signals.

25. An ultrasonic imaging device comprising:
an ultrasonic array and beam-former that transmits an ultrasonic signal;
an ultrasonic receiving array that receives ultrasonic echoes, the ultrasonic receiving array generating oversampled signal data based on the ultrasonic echoes; and
at least one processor configured to perform a robust Hermetic Transform on the echoes to produce an image, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \tag{a}$$

$$\underline{H} = \underline{\Sigma}^K \underline{\Omega}; \text{ and} \tag{b}$$

$$\underline{\sigma} = [(\underline{\Sigma} + \underline{N}_1)(\underline{\Sigma} + \underline{N}_2) \ldots]. \tag{c}$$

26. The device of claim 25, wherein the at least one processor performs Hermetic Matched Filtering to obtain a propagation delay measurement.

27. The device of claim 25, wherein the at least one processor performs the robust Hermetic Transform as a frequency analysis to obtain Doppler frequency shift measurements.

28. The device of claim 25, wherein the transmitting and receiving arrays are not co-located.

29. The device of claim 25, further comprising a filter that transmits pulsed signals to enhance specific resonance modes to enhance image resolution of object characteristics.

30. A method of ultrasonic imaging comprising:
transmitting an ultrasonic signal;
receiving ultrasonic echoes, wherein receiving the ultrasonic echoes comprises generating oversampled signal data based on the ultrasonic echoes; and
performing a robust Hermetic Transform on the echoes to produce an image, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \tag{a}$$

$$\underline{H} = \underline{\Sigma}^K \underline{\Omega}; \text{ and} \tag{b}$$

$$\underline{\sigma} = [(\underline{\Sigma} + \underline{N}_1)(\underline{\Sigma} + \underline{N}_2) \ldots]. \tag{c}$$

31. The method of claim 30, further comprising performing Hermetic Matched Filtering to obtain a propagation delay measurement.

32. The method of claim 30, further comprising performing the robust Hermetic Transform as a frequency analysis to obtain Doppler frequency shift measurements.

33. The method of claim 30, further comprising transmitting pulsed signals to enhance specific resonance modes to enhance image resolution of object characteristics.

34. The method of claim 30, further comprising performing tomographic imaging through at least one of absorption, diffraction, or time of flight.

35. The method of claim 30, further comprising performing at least one of for tissue heating, ultrasonic neuromodulation, lithotripsy, or low-intensity pulsed ultrasound.

36. An imaging device comprising:
a scanner having a receiver array that generates oversampled image data, the receiver array being associated with a plurality of channels; and
at least one processor configured to apply Hermetic Matched Filtering based on a robust Hermetic Transform to each channel of the plurality of channels and create beams for additional spatial filtering and signal separation via a time-delay beamforming approach to produce an image, the robust Hermetic Transform comprising solutions to a Moore-Penrose Pseudo-Inverse performed with a Singular Value Decomposition according to the following equations:

$$\underline{\Sigma}^H \underline{\Omega} \underline{\sigma} = \underline{\rho}; \tag{a}$$

$$\underline{H} = \underline{\Sigma}^K \underline{\Omega}; \text{ and} \tag{b}$$

$$\underline{\sigma} = [(\underline{\Sigma} + \underline{N}_1)(\underline{\Sigma} + \underline{N}_2) \ldots]. \tag{c}$$

37. An imaging method comprising apply a Hermetic Matched Filtering to each channel of a receiver array and creating beams for additional spatial filtering and signal separation via a time-delay beamforming approach to produce an image.

* * * * *